United States Patent [19]

Paspek et al.

[11] Patent Number: 5,186,817
[45] Date of Patent: Feb. 16, 1993

[54] PROCESS FOR SEPARATING EXTRACTABLE ORGANIC MATERIAL FROM COMPOSITIONS COMPRISING OIL-IN-WATER EMULSIONS COMPRISING SAID EXTRACTABLE ORGANIC MATERIAL AND SOLIDS

[75] Inventors: Stephen C. Paspek, Broadview Hts.; Jeffrey B. Hauser, Middleburgh Hts.; Christopher P. Eppig, Cleveland Hts., all of Ohio

[73] Assignee: The Standard Oil Company, Cleveland, Ohio

[21] Appl. No.: 686,278

[22] Filed: Apr. 15, 1991

Related U.S. Application Data

[63] Continuation of Ser. No. 513,107, Apr. 3, 1990, abandoned, which is a continuation-in-part of Ser. No. 441,110, Nov. 30, 1989, abandoned, which is a continuation-in-part of Ser. No. 320,865, Mar. 7, 1989, Pat. No. 4,885,079, which is a continuation of Ser. No. 906,727, Sep. 12, 1986, abandoned, said Ser. No. 513,107, is a continuation-in-part of Ser. No. 343,395, Apr. 25, 1989, abandoned, which is a continuation of Ser. No. 71,433, Jul. 8, 1987, Pat. No. 4,824,555, said Ser. No. 513,107, is a continuation-in-part of Ser. No. 278,967, Dec. 2, 1988, Pat. No. 4,981,579.

[51] Int. Cl.$^5$ .............................................. C10G 33/04
[52] U.S. Cl. .................................... 208/188; 208/314; 208/323; 208/336; 208/337; 210/108
[58] Field of Search .............. 208/188, 314, 323, 336, 208/337; 210/708

[56] References Cited

U.S. PATENT DOCUMENTS 2,272,372  2/1942  Hixon et al. ........................ 196/13
2,330,054  9/1943  Hilshman .

(List continued on next page.)

FOREIGN PATENT DOCUMENTS 260064  3/1988  European Pat. Off. .
0260064  3/1988  European Pat. Off. .

(List continued on next page.)

OTHER PUBLICATIONS

European Search Report Issued in European Application No. 89312196.2 on May 27, 1991.
Shell Oil Company Letter of Jan. 8, 1990 to EPA (List continued on next page.)

Primary Examiner—Theodore Morris
Assistant Examiner—William C. Diemler
Attorney, Agent, or Firm—Larry W. Evans; Teresan W. Gilbert

[57] ABSTRACT

This invention provides for a process for separating extractable organic material from a feed composition comprising an oil-in-water emulsion comprising a continuous aqueous phase, a discontinuous organic liquid phase comprising said extractable organic material, and solids dispersed in said emulsion, the process comprising the steps of:

(I) mixing said feed composition with sufficient shear to convert said feed composition to a water-in-oil emulsion; and (II) contacting said water-in-oil emulsion with at least one organic solvent, said organic solvent being capable of forming with said emulsion a system comprising at least two phases and being capable of dissolving at least about ten parts of said extractable organic material per million parts of said organic solvent at the temperature wherein at least about 50% by weight of said solvent boils at atmospheric pressure; forming a system comprising at least two phases, one of said phases being an emulsion phase comprising said emulsion and the other of said phases being a solvent phase comprising said solvent; replacing at least part of said extractable organic material with part of said solvent, the replaced extractable organic material being dispersed in said solvent phase; and separating said emulsion phase from said solvent phase. In one embodiment, the inventive process includes the additional steps of: separating an effective amount of said organic solvent from said separated emulsion phase to cause separation of said separated emulsion phase into an organic-rich phase and a water-rich phase; and separating said organic-rich phase from said water-rich phase. The solids can be present in either the separated organic-rich phase or the separated water-rich phase. The invention provides for post-treatment procedures for separating any extractable organic material remaining intermixed with the solids using solvent extraction, incineration, wet oxidation, or pyrolysis techniques, or a combination thereof.

69 Claims, 3 Drawing Sheets

U.S. PATENT DOCUMENTS

| | | | |
|---|---|---|---|
| 2,748,055 | 5/1956 | Payne | 208/337 |
| 2,886,523 | 5/1959 | Claridge et al. | 208/312 |
| 2,964,465 | 12/1960 | Brown et al. | 208/314 |
| 3,249,532 | 5/1966 | Shiah | 208/321 |
| 3,492,365 | 1/1970 | Anderson et al. | 260/674 |
| 3,725,254 | 4/1973 | Wang | 208/314 |
| 3,755,154 | 8/1973 | Akabayashi et al. | 208/332 |
| 3,761,402 | 9/1973 | Atwood | 208/314 |
| 3,764,008 | 10/1973 | Darley et al. | 210/73 |
| 3,867,275 | 2/1975 | Gleim et al. | 208/8 |
| 3,883,420 | 5/1975 | Stone | 208/321 |
| 4,260,489 | 4/1981 | Greig et al. | 210/771 |
| 4,353,794 | 10/1982 | Winter et al. | 208/321 |
| 4,389,300 | 6/1983 | Mitchell | 208/11 LE |
| 4,428,829 | 1/1984 | Kosters | 208/314 |
| 4,501,671 | 2/1985 | Bagell | 210/781 |
| 4,519,848 | 5/1985 | Underwood | 134/34 |
| 4,664,788 | 5/1987 | Gir et al. | 208/415 |
| 4,675,101 | 6/1987 | Warzinski | 208/311 |
| 4,715,932 | 12/1987 | Misselhorn et al. | 203/43 |
| 4,824,555 | 4/1989 | Paspek et al. | 288/188 |
| 4,842,715 | 6/1989 | Paspek et al. | 258/13 |
| 4,885,079 | 12/1989 | Eppig et al. | 208/314 |

FOREIGN PATENT DOCUMENTS 0298610 1/1989 European Pat. Off. .
2033244 5/1980 United Kingdom .

OTHER PUBLICATIONS

RCRA Docket (OS-305), "Comments on RCRA Proposed Rules Land Disposal Restrictions for Third Scheduled Wastes—Federal Register", Nov. 22, 1989, p. 48372.

PROCESS FOR SEPARATING EXTRACTABLE ORGANIC MATERIAL FROM COMPOSITIONS COMPRISING OIL-IN-WATER EMULSIONS COMPRISING SAID EXTRACTABLE ORGANIC MATERIAL AND SOLIDS

This is a continuation of co-pending application Ser. No. 07/513,107 filed on Apr. 23, 1990 now abandoned which application is a continuation-in-part of U.S. application Ser. No. 07/441,110, filed Nov. 30, 1989, now abandoned which was a continuation-in-part of U.S. application Ser. No. 320,865, filed Mar. 7, 1989, now U.S. Pat. No. 4,885,079, which was a continuation of U.S. application Ser. No. 906,727, filed Sep. 12, 1986, now abandoned. This application Ser. No. 513,107 is also a continuation-in-part of U.S. application Ser. No. 07/343,395, filed Apr. 25, 1989, now abandoned, which was a continuation of U.S. application Ser. No. 07/071,433, filed Jul. 9, 1987 (now U.S. Pat. No. 4,824,555). This application Ser. No. 513,107 is also a continuation-in-part of U.S. application Ser. No. 278,967, filed Dec. 2, 1988, now U.S. Pat. No. 4,981,579. The disclosures of said prior applications are incorporated herein by reference in their entireties.

TECHNICAL FIELD

This invention relates to a process for separating extractable organic material from a composition comprising an oil-in-water emulsion comprising a continuous aqueous phase, a discontinuous organic phase comprising said extractable organic material, and solids dispersed in said emulsion. The inventive process involves: inverting the emulsion to form a water-in-oil emulsion; contacting the emulsion with at least one solvent to form a system comprising at least two phases, one of the phases being an emulsion phase and the other phase being a solvent phase; replacing at least part of the extractable organic material with solvent, the replaced extractable organic material being dispersed or dissolved in the solvent phase; and separating the emulsion phase from the solvent phase. The solids are present in the emulsion phase, and the invention provides for separation of these solids from such phase. The invention is particularly suitable for separating undesirable or hazardous organic materials (e.g., three-, four- and/or five-ring aromatic compounds) from solids-stabilized oil-in-water emulsions (e.g., petroleum refinery waste).

BACKGROUND OF THE INVENTION

Stable oil-in-water emulsions have been a problem in many areas of the petroleum industry. In the production of oil under water-flood conditions, oil-in-water emulsions are obtained from the production wells. These emulsions must be broken in order to recover the oil in useful form. When cleaning oil tanker bilges, oil-in-water emulsions frequently form and present disposal problems. In the processing of crude oils, such as by desalting, stable emulsion layers are formed in the desalter resulting in the waste of valuable oil and the creation of a disposal problem. Oily wastewater streams that are generated at many different refinery processing units often contain solids that are intermixed with hazardous organic materials that are regulated under the Resource, Conservation and Recovery Act (RCRA). The hazardous organic materials must be separated from the solids before the solids can be land disposed or land treated.

The stability of oil-in-water emulsions such as those described above is increased by the presence of dispersed solids. It is recognized that the stability of oil-water-solids emulsions is a function of the composition, i.e., the relative amounts of oil, water and solids in the mixture as well as the type of oil and solids. The breaking of such emulsions requires alteration of this ratio. The addition of miscible hydrocarbons to water-in-oil generally only serves to swell the emulsion phase and does not lead to emulsion breaking. Thus, simple techniques such as diluting the emulsion with naphtha do not lead to the desired result. Removal of solids by filtration has a tendency to break the emulsion, but generally, since the emulsions are so viscous, filtration is extremely difficult. Centrifugation of oil-water-solid emulsions results in rather poor separation.

U.S. Pat. No. 2,235,639 describes a procedure for the resolution of oil and water emulsions by adding a liquefied gas (such as ethane, butane, propane, etc.) to the emulsion. The liquefied gas is added to the emulsion under sufficient pressure to prevent vaporization of the gas. While the mixture is under pressure, the emulsion breaks, and water settles from the emulsion leaving the oil in a purified condition. While still under pressure, water is withdrawn and the oil is transferred to a secondary zone where it is heated to volatilize the hydrocarbon gas.

U.S. Pat. Nos. 2,383,362 and 2,383,363 describe processes for the separation of water from hydrocarbon-water emulsions. More particularly, these patents relate to the breaking of tar emulsions and the separation of the water from the tar component by mixing a liquefied normally gaseous hydrocarbon solvent with the emulsions. The '362 patent is directed primarily to the use of propane whereas the '363 patent utilizes pentane as the liquid phase hydrocarbon.

U.S. Pat. No. 3,696,021 describes the separation of oily sludges by mixing the sludges with a light hydrocarbon to form an oil-hydrocarbon phase and a water-solids phase. The oil-hydrocarbon phase then is heated to an elevated temperature to remove the light hydrocarbons which may be recycled, and the oil is recovered for further use. The light hydrocarbons disclosed as being suitable for use in the process include propane, butane, pentane, as well as mixtures and isomers thereof.

SUMMARY OF THE INVENTION

This invention provides for a process for separating extractable organic material from a feed composition comprising an oil-in-water emulsion comprising a continuous aqueous phase, a discontinuous organic liquid phase comprising said extractable organic material, and solids dispersed in said emulsion, the process comprising the steps of:

(I) mixing said feed composition with sufficient shear to convert said feed composition to a water-in-oil emulsion; and (II) contacting said water-in-oil emulsion with at least one organic solvent, said organic solvent being capable of forming with said emulsion a system comprising at least two phases and being capable of dissolving at least about ten parts of said extractable organic material per million parts of said organic solvent at the temperature wherein at least about 50% by weight of said solvent boils at atmospheric pressure; forming a system comprising at least two phases, one of said phases being an emulsion phase comprising said emulsion and the other of said phases being a solvent phase comprising said solvent; replacing at least part of said extractable organic material with part of said solvent, the replaced extractable organic material being dispersed in said solvent phase; and separating said emulsion phase from said solvent phase.

In one embodiment, the inventive process includes the additional steps of: separating an effective amount of said organic solvent from said separated emulsion phase to cause separation of said separated emulsion phase into an organic-rich phase and a water-rich phase; and separating said organic-rich phase from said water-rich phase. The solids can be present in either the separated organic-rich phase or the separated water-rich phase. The invention provides for post-treatment procedures for separating any extractable organic material remaining intermixed with the solids using solvent extraction, incineration, wet oxidation, or pyrolysis techniques, or a combination thereof.

DESCRIPTION OF THE PREFERRED EMBODIMENTS

Figure 1:
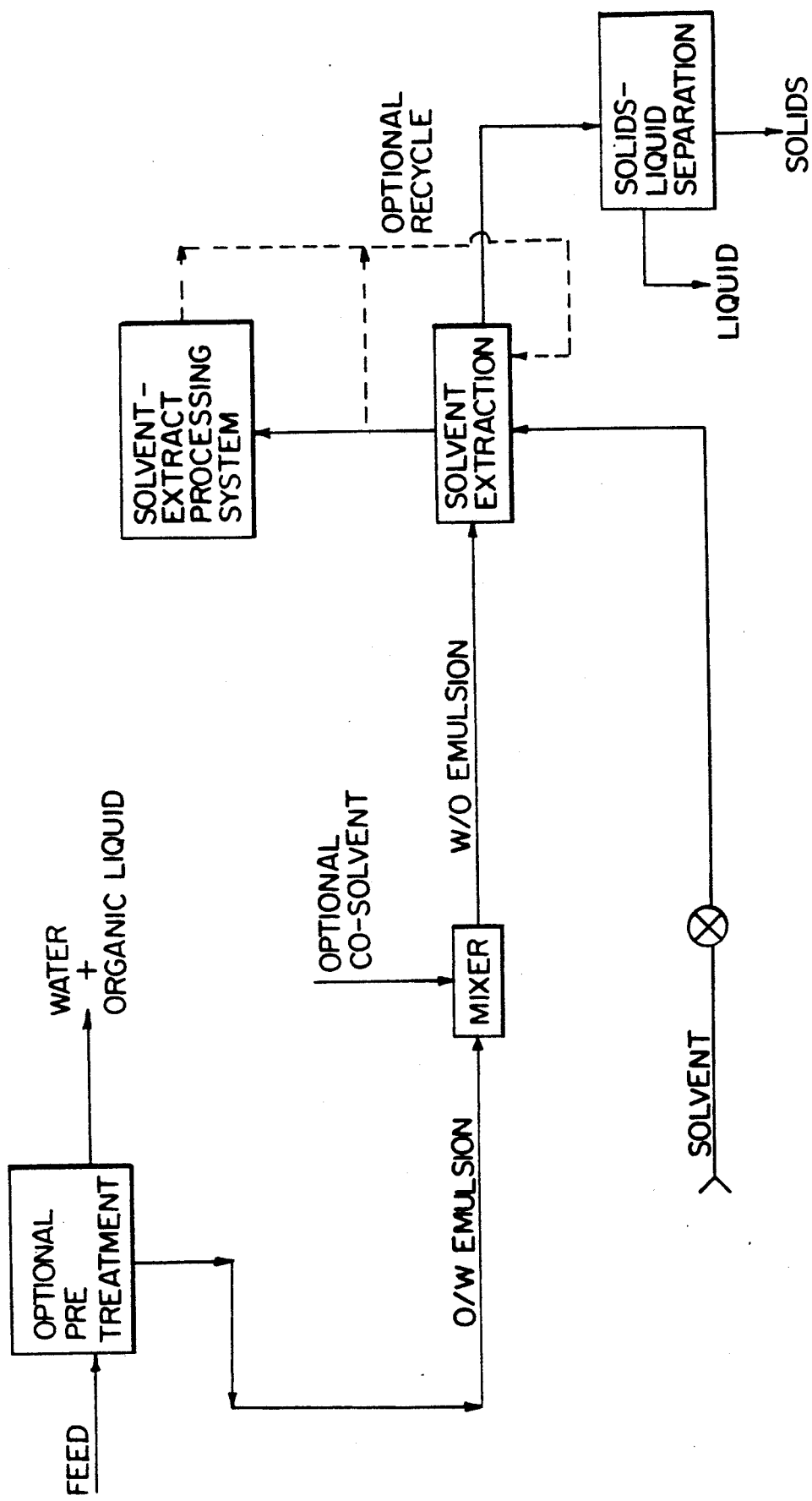
FIG. 1 is a flow sheet illustrating one embodiment of the invention wherein a process is used to separate extractable organic material from a feed composition comprising an oil-in-water emulsion comprising a continuous aqueous phase, a discontinuous organic phase comprising said extractable organic material, and solids dispersed in said emulsion.

The term "oil-in-water" emulsion (abbreviated "o/w" emulsion) refers to emulsions wherein the continuous phase is aqueous and the discontinuous phase is organic, the discontinuous organic phase being dispersed in the continuous aqueous phase.

The term "water-in-oil" emulsion (abbreviated "w/o" emulsion) refers to emulsions wherein the continuous phase is organic and the discontinuous phase is aqueous, the discontinuous aqueous phase being dispersed in the continuous organic phase.

The term "hazardous organic material" refers to organic materials or combinations of organic materials which are "listed" by the EPA as hazardous, or which exhibit ignitability, corrosivity or reactivity, or are considered toxic pursuant to relevant governmental rules or regulations. Examples include three-, four- and five-ring aromatic compounds. These hazardous organic materials are extractable organic materials.

The term "extractable organic material" refers to any organic material present in the feed compositions treated in accordance with the inventive process that can be extracted using the solvent extraction procedures provided by said process. Examples include petroleum oil as well as hazardous organic materials. The extractable organic material is typically in a liquid state at the pressure and temperature employed in the operation of the inventive process, although part of such extractable organic material may be in a solid state at such pressure and temperature.

Feed Compositions

The feed compositions that can be treated in accordance with the invention comprise oil-in-water emulsions which comprise a continuous aqueous phase, a discontinuous organic or oil phase comprising said extractable organic material, and solids dispersed or suspended in said emulsion. These feed compositions can be in the form of emulsion mixtures wherein in parts of the emulsion the organic phase is the continuous phase and a discontinuous aqueous phase is dispersed in said organic phase, while in other parts of the emulsion the aqueous phase is the continuous phase and a discontinuous organic phase is dispersed in the aqueous phase.

These feed compositions can be derived from a variety of sources within the petroleum industry. For example, these feed compositions may be obtained from production wells under waterflood conditions. These feed compositions include oil-in-water emulsions that are formed during the cleaning of oil tanker bilges. A significant source is from the desalting of crude oil wherein stable emulsion layers form in the desalter which, if not broken, must be disposed and results in the waste of valuable oil. Another significant source are the oily wastewater streams that are generated at many different refinery processing units. These oily wastewater streams often contain solids intermixed with hazardous organic materials that are regulated under RCRA and must be removed before the solids can be land disposed or land treated.

The solids can be in any form, but in many instances are in the form of particulate solids. In one embodiment of the invention, the solids are fine particulates. These fine particulates can have average diameters of less than about 50 microns. The solids can be porous, and these porous solids can be filled with liquid (e.g., water, organic liquid). The solids that are hydrophilic will generally be in the aqueous phase, and the solids that are hydrophobic will generally be in the organic phase. The solids can be organic, inorganic or a mixture thereof. The presence of these solids in the feed composition makes it particularly difficult to break the emulsion, and therefore, it is difficult to process such emulsion for the purpose of recovering oil, and extracting undesirable or hazardous organic materials from the solids to render such solids suitable for land disposal.

The feed compositions can contain varying amounts of organic liquids (e.g., oil), water and solids. These feed compositions can also contain hazardous organic materials, as well as undesirable metals and/or metal compounds (e.g., EPA listed metals such as nickel, chromium and the like). For example, these feed compositions may typically comprise:
(i) from about 10% to about 90% by weight water;
(ii) from about 10% to about 90% by weight organic liquid;
(iii) from about 0.01% to about 50% by weight solids;

(iv) up to about 10% by weight metals and/or metal compounds; and (v) up to about 50% by weight hazardous organic material.

Solvents and Co-Solvents

The inventive process involves the use of an optional co-solvent or co-solvent mixture during step (I) and one or more solvents or solvent mixtures during step (II). These solvents are of two distinct types and are identified below as Solvent A and Solvent B.

Solvent A

Solvent A is an organic solvent capable of dissolving at least about ten parts of at least one of the extractable organic materials in the feed composition being treated per million parts of said organic solvent at the temperature wherein at least about 50% by weight of said organic solvent boils at atmospheric pressure. This solvent is preferably selected from those organic solvents which: dissolve hydrocarbon oil and heavy residual organics such as asphaltenes at modest temperatures (e.g., in the range of about 30° F. to about 400° F., preferably about 200° F. to about 300° F.) and at moderate pressures (e.g., below about 500 psig); and can be separated from water and such hydrocarbon oil and heavy residual organics using conventional separation techniques.

These solvents include aliphatic compounds, aromatic compounds, cycloaliphatic compounds, aliphatic-substituted aromatic compounds, cycloaliphatic-substituted aromatic compounds, aliphatic-substituted cycloaliphatic compounds, and mixtures thereof. These compounds include substantially hydrocarbon compounds as well as purely hydrocarbon compounds. The term "substantially hydrocarbon" is used herein to mean that the compounds contain no non-hydrocarbon substituents or non-carbon atoms that significantly affect the hydrocarbon characteristics or properties of such compounds relevant to their use herein as solvents.

The aromatic compounds can be mononuclear (e.g., benzene) or polynuclear (e.g., naphthalene, anthracene, etc.). The aliphatic substituents on the aromatic compounds can be straight chain or branched-chain hydrocarbon groups of 1 to about 3 carbons, cyclic groups of about 3 to about 6 carbons, or mixtures thereof. The aromatic compounds can be mono-substituted or poly-substituted. Examples of such substituted aromatic compounds include toluene, the xylenes, ethyl benzene, cyclohexyl benzene, etc.

The cycloaliphatic compounds can have from about 3 to about 6 ring carbon atoms, preferably 5 or 6 ring carbon atoms, and can be saturated or unsaturated. Examples include cyclopropane, cyclobutane, cyclopentane, cyclopentene, 1,3-cyclopentadiene, cyclohexane, cyclohexene, 1,3-cyclohexadiene, etc. The aliphatic substituents on the aliphatic-substituted cycloaliphatic compounds can be straight chain hydrocarbon groups of 1 to about 6 carbon atoms, preferably 1 to about 3 carbon atoms. The rings of the cycloaliphatic compounds can be mono-substituted or poly-substituted. Examples include methylcyclopentane, methylcyclohexane, 1,3-dimethylcyclohexane, 3-ethylcyclopentene, 3,5-dimethylcyclopentene, etc.

Solvent A preferably has an initial boiling point in the range of about 0° F. to about 500° F., and a final boiling point in the range of about 200° F. to about 1000° F. at atmospheric pressure. These solvents can have an aromatic content in excess of about 25% by weight, and in many instances they have an aromatic content in excess of about 50% by weight. In one embodiment, this solvent has an initial boiling point in the range of about 50° F. to about 150° F., and a final boiling point in the range of about 200° F. to about 300° F. In one embodiment, this solvent has an initial boiling point in the range of about 180° F. to about 280° F., and a final boiling point in the range of about 325° F. to about 425° F. In one embodiment, this solvent has an initial boiling point in the range of about 200° F. to about 325° F., and a final boiling point in the range of about 425° F. to about 525° F. In one embodiment, this solvent has an initial boiling point in the range of about 300° F. to about 500° F., and a final boiling point in the range of about 650° F. to about 850° F. In one embodiment, at least about 50% by weight, more preferably at least about 75% by weight, more preferably at least about 90% by weight, of this solvent boils at a temperature below about 750° F. at atmospheric pressure, and all or substantially all of said solvent boils at a temperature below about 1000° F. at atmospheric pressure. In one embodiment this solvent has an initial boiling point in the range of about 200° F. to about 325° F., preferably about 260° F. to about 290° F., a 90% by weight boiling point in the range of about 350° F. to about 450° F., preferably about 380° F. to about 420° F. (that is, 90% by weight of the solvent boils at a temperature below about 350° F. to about 450° F. at atmospheric pressure), and a final boiling point in the range of about 425° F. to about 525° F., preferably about 460° F. to about 490° F.; this solvent preferably contains in excess of about 50% by weight aromatics, more preferably in excess of about 75% by weight aromatics, more preferably in excess of about 90% by weight aromatics. In one embodiment this solvent has an initial boiling point in the range of about 300° F. to about 500° F., preferably about 360° F. to about 420° F., a final boiling point in the range of about 650° F. to about 850° F., preferably about 720° F. to about 780° F.; this solvent preferably has an aromatics content of in excess of about 50% by volume, preferably in the range of about 50% to about 90% by volume, more preferably about 60% to about 80% by volume.

Solvent A can be an aromatic or aromatic-rich solvent that is readily available from a refinery system such as, for example, one or more reformates (e.g., light reformate, heavy reformate, etc.) that are produced by reformers in a typical refinery system. A typical light reformate has an initial boiling point in the range of about 50° F. to about 150° F., a final boiling point in the range of about 250° F. to about 350° F., and contains benzene and toluene. A typical heavy reformate has an initial boiling point in the range of about 250° F. to about 350° F., a final boiling point in the range of about 450° F. to about 550° F., and contains toluene, ethylbenzene, o-xylene and p-xylene.

Solvent A can be a middle distillate such as fuel oil, kerosene and the like. Solvent A can be a straight-run or process-generated distillate (e.g., naphtha, kerosene or gas oil). Solvent A can be a cracked product such as coker distillate. Solvent A can be a natural gas condensate comprising hydrocarbons of about 7 to about 12 carbon atoms and having an aromatic and/or naphthene content of about 5% to about 90% by weight.

Solvent B

Solvent B is an organic solvent that is capable of forming with the water-in-oil emulsion that is treated in accordance with step (II) of the inventive process a system comprising at least two phases. That is, Solvent B must have a different density than said emulsion and must be at least partially immiscible with said emulsion. Solvent B is also capable of dissolving at least about ten parts of the extractable organic material in said emulsion per million parts of Solvent B at the temperature wherein at least about 50% by weight of Solvent B boils at atmospheric pressure. In one embodiment, Solvent B is capable of dissolving at least about ten parts of Solvent A per million parts Solvent B at the temperature wherein at least about 50% by weight of Solvent B boils at atmospheric pressure. In one embodiment, Solvent B is capable of dissolving at least about ten parts of hydrocarbon oil per million parts of Solvent B at the temperature wherein at least about 50% by weight of Solvent B boils at atmospheric pressure. In one embodiment, Solvent B is more volatile than Solvent A. Solvent B is preferably economically recoverable from the separated emulsion produced in accordance with step (II) of the inventive process.

Preferred solvents include aliphatic hydrocarbons having from 2 to about 9 carbon atoms, more preferably from about 3 to about 7 carbon atoms, more preferably from about 3 to about 5 carbon atoms; cycloaliphatic and hydrocarbon-substituted cycloaliphatic hydrocarbon compounds of from 3 to about 9 carbon atoms, more preferably 3 to about 7 carbon atoms, more preferably 3 to about 5 carbon atoms; halohydrocarbons of preferably from 1 to about 9 carbon atoms, more preferably 1 to about 5 carbon atoms, more preferably 1 to about 3 carbon atoms; and mixtures of two or more of any of the foregoing.

Examples of such solvents include propane, cyclopropane, propylene, n-butane, isobutane, cyclobutane, butene (e.g., butene-1, cis-butene-2, trans-butene-2), butadiene (e.g., 1,3-butadiene), isobutylene, n-pentane, isopentane, neopentane, cyclopentane, pentene (e.g., pentene-1, cis-pentene-2, etc.), cyclopentene, pentadiene(e.g., 1,3-pentadiene, etc.), cyclopentadiene, cyclohexane, cyclohexene, cyclohexadiene, methylene chloride, dichlorodifluoromethane, trichlorofluoromethane, cloroethane, trichloroethane, dichlorotetrafluoroethane, trichloroethylene, tetrafluoroethylene, chloropropane, chlorobutane, chloropentane, dichloropentane, and mixtures of two or more thereof.

Solvent B can be a solvent mixture comprising one or more of the foregoing compounds and up to about 50% by weight, more preferably up to about 30% by weight, more preferably up to about 10% by weight of one or more aromatic or hydrocarbon-substituted aromatic compounds of up to about 12 carbon atoms. Examples of such aromatic and hydrocarbon-substituted aromatic compounds include benzene, toluene, xylene, naphthalene, etc.

Solvent B can be a mixture made up primarily of hydrocarbon compounds or substantially hydrocarbon compounds of from about 3 to about 5 carbon atoms (e.g., natural gas condensates of about 3 to about 5 carbon atoms) and/or from about 5 to about 7 carbon atoms (e.g., gas well condensates such as those comprising hydrocarbons of from about 5 to about 7 carbon atoms). Solvent B can be straight-run gasoline.

Solvent B can be liquified petroleum gas (LPG). Examples of commercial grades of LPG include Commercial Propane, Commercial Butane, Commercial Propane-Butane Mixtures, Special Duty Propane and Propane HD-5. Straight-run gasoline is useful. Mixtures of two or more of the foregoing solvents can be used.

Solvent Selection

The co-solvent or co-solvent mixture, if any, that is used during Step (I) of the inventive process, and the solvents or solvent mixtures used in Step (II) of said process preferably have solubility parameters that closely match the solubility parameter of the extractable organic material that is to be separated from the feed composition. The solubility parameter of a solvent is a measurement for quantifying the "strength" of a solvent. That is, the solubility parameter is a measure of the ability of a solvent to dissolve a solute.

Single parameter solubility parameters are useful in approximating the solubility of a hydrocarbon solute in a hydrocarbon solvent. Single parameter solubility parameters can be represented by delta, defined as the square root of the molecular cohesive energy ($-E$) per unit volume of solvent, and have the units $(cal/ml)^{\frac{1}{2}}$. Table I is a list of single parameter solubility parameters for various solvents that are useful with the invention. (The molar volume for each of such solvents is also indicated in Table I ; such molar volume is useful in calculating the solubility parameter for mixtures of solvents as discussed below.)

TABLE I

|  | Delta $(cal./ml.)^{\frac{1}{2}}$ | Molar Volume (ml./gm-mole) |
|---|---|---|
| Ethane | 6.05 | 68 |
| Propane | 6.40 | 84 |
| i-Butane | 6.73 | 105.5 |
| n-Butane | 6.73 | 101.4 |
| i-Pentane | 7.02 | 117.4 |
| n-Pentane | 7.02 | 116.1 |
| neo-Pentane | 7.02 | 123.3 |
| n-Hexane | 7.27 | 131.6 |
| n-Heptane | 7.43 | 147.5 |
| n-Octane | 7.55 | 163.5 |
| n-Nonane | 7.65 | 179.6 |
| n-Decane | 7.72 | 196.0 |
| n-Undecane | 7.79 | 212.2 |
| n-Dodecane | 7.84 | 228.6 |
| n-Hexadecane | 7.99 | 294.1 |
| Ethylene | 6.08 | 61 |
| Propylene | 6.43 | 79 |
| Cyclopentane | 8.11 | 94.7 |
| Methylcyclopentane | 7.85 | 113.1 |
| Cyclohexane | 8.20 | 108.7 |
| Methylcyclohexane | 7.83 | 128.3 |
| Benzene | 9.16 | 89.4 |
| Toluene | 8.92 | 106.8 |
| o-Xylene | 8.99 | 121.2 |
| m-Xylene | 8.82 | 123.5 |
| p-Xylene | 8.77 | 124.0 |

The single parameter solubility parameter for a mixture of solvents is the weighted mean of the pure component solubility parameters and can be calculated using the formula $$\text{Delta}_{mix} = \frac{\Sigma X_i V_i \text{Delta}_i}{\Sigma X_i V_i}$$

wherein: Delta$_{mix}$ is the solubility parameter of the mixture; $X_i$ is the mole fraction of pure component i; $V_i$ is the molar volume of pure component i; and Delta$_i$ is the solubility parameter of the pure component i. For example, a list of single parameter solubility parameters for various mixtures of toluene and pentane is provided in Table II:

TABLE II

| Mole Fraction Toluene | Mole Fraction n-pentane | Delta (cal./ml.)$^{\frac{1}{2}}$ |
| --- | --- | --- |
| 0.0 | 1.0 | 7.02 |
| 0.1 | 0.9 | 7.21 |
| 0.2 | 0.8 | 7.40 |
| 0.3 | 0.7 | 7.59 |
| 0.4 | 0.6 | 7.78 |
| 0.5 | 0.5 | 7.97 |
| 0.6 | 0.4 | 8.16 |
| 0.7 | 0.3 | 8.35 |
| 0.8 | 0.2 | 8.54 |
| 0.9 | 0.1 | 8.73 |
| 1.0 | 0.0 | 8.92 |

In one embodiment of the invention, a mixture of two solvents are used during steps (I) and/or (II) of the inventive process. The single parameter solubility parameter for one solvent is preferably in the range of about 7 to about 14 (cal./ml.)$^{\frac{1}{2}}$ at 70° F. The single parameter solubility parameter for the other solvent is preferably in the range of about 5.5 to 8.5 (cal./ml.)$^{\frac{1}{2}}$ at 70° F. The single parameter solubility parameter for the solvent mixture is preferably in the range of about 6 to about 13 (cal./ml.)$^{\frac{1}{2}}$ at 70° F.

The single parameter solubility parameter that is preferred for the co-solvent used during step (I), if any is used, and the solvent that is used during step (II) of the inventive process is dependent upon the single parameter solubility parameter of the particular extractable organic material that is to be separated from the feed composition. In one embodiment of the invention, the single parameter solubility parameters of the co-solvent and the solvent match the single parameter solubility parameter of such extractable organic material within reasonable limitations in order to provide the desired level of extraction. The single parameter solubility parameters of the co-solvent and solvent are preferably within about ±2 (cal./ml.)$^{\frac{1}{2}}$ at 70° F. of the single parameter solubility parameter at 70° F. of the extractable organic material that is to be separated. More preferably, the single parameter solubility parameter of the co-solvent and solvent is within about ±1.5 (cal./ml.)$^{\frac{1}{2}}$ at 70° F. of the single parameter solubility parameter of the extractable organic material, more preferably within about ±1 (cal./ml.)$^{\frac{1}{2}}$, more preferably within about ±0.5 (cal./ml.)$^{\frac{1}{2}}$, more preferably within about ±0.25 (cal./ml.)$^{\frac{1}{2}}$.

If the extractable organic material that is to be separated consists of a mixture of several organic materials, then in order to provide the most effective extraction, it is preferred to match the solubility parameter of the co-solvent and/or solvent with the solubility parameter of the more difficult to extract organic materials in the feed composition. For example, in a typical refinery waste, the more difficult to extract organic materials are typically heavy oils and asphaltenes. In many instances, such heavy oils and asphaltenes have single parameter solubility parameters of about 8 to about 11 (cal./ml.)$^{\frac{1}{2}}$ at 70° F., and thus the co-solvent and/or solvent mixtures that is preferred for separating these materials have single parameter solubility parameters at 70° F. preferably in the range of about 6 to about 13 (cal./ml.)$^{\frac{1}{2}}$, more preferably about 7 to about 12 (cal./ml.)$^{\frac{1}{2}}$, more preferably about 8 to about 11 (cal./ml.)$^{\frac{1}{2}}$.

The single parameter solubility parameter of an extractable organic material can be determined experimentally by dispersing samples of the extractable organic material in a series of solvents having known single parameter solubility parameters varying over a predetermined range, and measuring the level of dissolution of extractable organic material in each sample. The solvent exhibiting the highest degree of dissolution of extractable organic material therein has the single parameter solubility parameter that matches the single parameter solubility parameter of the extractable organic material most closely. For example, an extractable organic material having a single parameter solubility parameter of about 8 (cal./ml.)$^{\frac{1}{2}}$ that is dissolved in samples of each of the solvents listed in Table I would in general exhibit the highest degree of dissolution in the solvents having single parameter solubility parameters of about 7.5 to about 8.5 (cal./ml.)$^{\frac{1}{2}}$.

Two-parameter solubility parameters are useful in approximating the solubility of a solute in a solvent when the solute (or at least one of the solutes in a mixture of solutes) and/or solvent (or at least one of the solvents in a solvent mixture) contain appreciable quantities of non-hydrocarbon groups (e.g., halo, hydroxy, etc.). Examples of such solutes include the asphaltenes. Examples of such solvents include methylene chloride, dichlorodifluoromethane, trichlorofluoromethane, cloroethane, trichloroethane, dichlorotetrafluoroethane, trichloroethylene, tetrafluoroethylene, chloropropane, chlorobutane, chloropentane, dichloropentane, and mixtures of two or more thereof. With such two-parameter solubility parameters, each solvent (or solvent mixture) and each solute (or mixture of solutes) has two solubility parameters, namely, Delta$_r$ and Delta$_v$. Delta$_r$ and Delta$_v$ for many organic materials are known and readily available from the literature. Delta$_r$ for a solvent mixture or solute mixture is the weighted mean of the pure component Delta$_r$'s for the mixture and is calculated using the formula:

$$\text{Delta}_{r(mix)} = \frac{\Sigma X_i V_i \text{Delta}_{r(i)}}{\Sigma X_i V_i}$$

wherein: Delta$_{r(mix)}$ is the solubility parameter r of the mixture; $X_i$ is the mole fraction of pure component i; $V_i$ is the molar volume of pure component i; and Delta$_{r(i)}$ is the solubility parameter r of the pure component i. Delta$_v$ for a solvent mixture or solute mixture is the weighted mean of the pure component Delta$_v$'s for the mixture and is calculated using the formula:

$$\text{Delta}_{v(mix)} = \frac{\Sigma X_i V_i \text{Delta}_{v(i)}}{\Sigma X_i V_i}$$

wherein: Delta$_{v(mix)}$ is the solubility parameter v of the mixture; $X_i$ is the mole fraction of pure component i; $V_i$ is the molar volume of pure component i; and Delta$_{v(i)}$ is the solubility parameter v of the pure component i. The difference between the two-parameter solubility parameters for the solvent or solvent mixture used in accordance with the invention and the extractable organic material to be separated in accordance with the invention can be determined using the formula:

$$A = ((\text{Delta}_{r(s)} - \text{Delta}_{r(e)})^2 + (\text{Delta}_{v(s)} - \text{Delta}_{v(e)})^2)^{\frac{1}{2}}$$

wherein: A is the difference between the two-parameter solubility parameters for the solvent or solvent mixture of the invention and the extractable organic material to be separated; Delta$_{r(s)}$ is Delta$_r$ for the solvent mixture;

Delta$_{r(e)}$ is Delta$_r$ for the extractable organic material; Delta$_{v(s)}$ is Delta$_v$ for the solvent or solvent mixture; and Delta$_{v(e)}$ is Delta$_v$ for the extractable organic material. In one embodiment of the invention, each of the solubility parameters Delta$_{r(s)}$, Delta$_{r(e)}$, Delta$_{v(s)}$ and Delta$_{v(e)}$ are determined at about 70° F. and A is preferably up to about 3 (cal./ml.)$^{\frac{1}{2}}$, more preferably up to about 2 (cal./ml.)$^{\frac{1}{2}}$, more preferably up to about 1 (cal./ml.)$^{\frac{1}{2}}$.

Three-parameter solubility parameters are also useful in approximating the solubility of a solute in a solvent. Three-parameter solubility parameters for many organic materials are known in the art. See, for example, Barton, Allan F. M., "CRC Handbook of Solubility Parameters and Other Cohesion Parameters", CRC Press Inc., 2000 Corporate Blvd., N.W., Boca Raton, Fla. 33431, Library of Congress Card No. 82-9653, which is incorporated herein by reference for its disclosure of solubility parameters of solvents used in accordance with this invention and extractable organic materials that are separated in accordance with this invention. The three parameter solubility parameters disclosed in this reference are referred to therein as Delta$_d$, Delta$_p$ and Delta$_h$, and are related to the single-parameter solubility parameters and two-parameter solubility parameters discussed above. Also disclosed in this reference for a number of organic materials is Delta$_t$, which corresponds to the single-parameter solubility parameter for such materials, and is equal to the square root of the sum of the squares of Delta$_d$, Delta$_p$ and Delta$_h$. That is, $$\text{Delta}_t = (\text{Delta}_d^2 + \text{Delta}_p^2 + \text{Delta}_h^2)^{\frac{1}{2}}$$

Thus, using the foregoing formula, the single parameter solubility parameter of a solvent or a solute can be determined if three-parameter solubility parameters for such solvent or solute are known.

The two-parameter solubility parameters for an organic material can be determined if the three-parameter solubility parameters for such material are known. In this regard, Delta$_r$ is equal to Delta$_h$, and Delta$_v$ is equal to the square root of the sum of the squares of Delta$_d$ and Delta$_p$. That is, $$\text{Delta}_r = \text{Delta}_h$$

$$\text{Delta}_v = (\text{Delta}_d^2 + \text{Delta}_p^2)^{\frac{1}{2}}$$

Thus, using the foregoing formula, the two-parameter solubility parameters for the solvents used in accordance with the invention and the extractable organic materials to be separated can be determined if the three-parameter solubility parameters for such materials are known.

Process

In one embodiment of the invention, the feed composition to be treated is optionally pretreated to remove some of the water and organic liquid (e.g., oil) prior to treatment in accordance with the inventive process. In this pretreating step, thermal and/or mechanical processing units can be used. Examples include vacuum filters, belt presses, filter presses, centrifuges, hydroclones, decanters, or a combination of the foregoing, the design of which are entirely conventional. A dryer to further de-water the feed composition can be used.

The feed composition (whether or not it is pretreated) is conveyed to a mixer for converting the feed composition from an oil-in-water emulsion to a water-in-oil emulsion using mixing with sufficient shear to effect emulsion inversion during step (I) of the inventive process. Typically high shear mixing is required to invert the emulsion. This mixing can be carried out using batch or semi-batch mixing or continuous in-line mixing techniques. The temperature employed during this step is preferably from about 32° F. to about 600° F., more preferably about 32° F. to about 250° F., more preferably about 40° F. to about 120° F. The pressure is dependent on temperature and should be sufficient to maintain at least about 70% by weight, more preferably at least about 80% by weight, more preferably at least about 90% by weight of the mixer contents (excluding solids) in liquid state. The pressure is preferably about atmospheric pressure to about 1000 psig, more preferably about atmospheric pressure to about 200 psig. Residence time in the mixer is preferably about one second to about one hour, more preferably about 0.1 to about 30 minutes, more preferably about 0.1 minute to about 5 minutes. The emulsion can be tested using conventional techniques (e.g., dilution, electrophoresis or microscopic examination) to determine whether inversion has been effected.

This inversion step can also be facilitated by mixing a co-solvent with the feed composition prior to and/or during step (I). This co-solvent can be one or more of Solvent A, one or more of Solvent B, or a mixture thereof. Addition of this co-solvent can be effected using standard mixing or blending techniques. The co-solvent is preferably added at a sufficient level to provide the feed composition with a liquid organic content of preferably from about 10% to about 90% by weight, more preferably about 20% to about 90% by weight, more preferably about 30% to about 90% by weight, based on the total weight of the feed composition.

The water-in-oil emulsion from step (I) is contacted with an effective amount of one or more of Solvent B during step (II) to from a system with at least two phases, one of the phases being an emulsion or emulsion-rich phase comprising the water-in-oil emulsion from step (I), and the other phase being a solvent or solvent-rich phase comprising the Solvent B added during step (II). The phases are maintained in contact with each other, preferably with mixing, until at least part of the extractable organic material in the emulsion phase is replaced by solvent from the solvent phase. Preferably all or substantially all of the extractable organic material in the emulsion phase is replaced by solvent. The replaced extractable organic material disperses or dissolves in the solvent phase. The temperature during step (II) is preferably from about 32° F. to about 600° F., more preferably about 32° F. to about 250° F., more preferably about 40° F. to about 120° F. The pressure is dependent on temperature and is preferably sufficient to maintain at least about 70%, more preferably at least about 80%, more preferably at least about 90% two-phase system (excluding solids) in liquid state. The pressure is preferably about atmospheric to about 1000 psig, more preferably about atmospheric to about 200 psig. Contact time between the emulsion phase and the solvent phase is preferably from about one second to about two hours, more preferably about one second to about one hour, more preferably about one second to about 30 minutes. The emulsion phase and the solvent phase are then separated using conventional separation techniques (e.g., decantation, centrifugation, extraction using a volatile solvent, flashing, vaporization, etc.).

The separated emulsion phase comprises solvent, solids and water, and any remaining extractable organic material not extracted during step (II). Step (II) can be repeated to extract additional extractable organic material from the separated emulsion phase.

The separated solvent phase comprises solvent and extracted organic material. If the amount of extracted organic material in the separated solvent phase is relatively low, the separated solvent phase can be recycled. The solvent and extract can be separated using standard techniques (e.g., distillation), and the solvent can be recycled. The extract can be disposed of or is available for subsequent use or treatment.

Extractable organic material remaining intermixed in the separated emulsion phase can be separated from the solids in said emulsion phase. This is done by separating an effective amount of organic solvent from the separated emulsion phase to cause separation of the separated emulsion phase into an organic-rich phase and a water-rich phase. That is, an effective amount of solvent is removed from the emulsion to break the emulsion. This is preferably accomplished by flashing or vaporizing the solvent using known techniques. The organic-rich phase is then separated from the water-rich phase using conventional techniques (e.g., decantation, centrifugation, extraction using a volatile solvent, etc.).

The solids that are hydrophilic will generally be dispersed in the water-rich phase. The water can be separated from such solids using conventional solids-water separation techniques (e.g., filtration, centrifugation, vaporization, etc.). These solids may contain extractable organic material intermixed therewith. Whether or not water is initially removed from such solids, extractable organic material can be separated from such solids using incineration, wet oxidation, pyrolysis or solvent extraction techniques, or a combination thereof.

The solids that are hydrophobic will generally be dispersed in the organic-rich phase. These solids can be separated from the organic-rich phase using conventional techniques (e.g., filtration, centrifugation, vaporization, etc.). These solids can contain extractable organic material intermixed therewith. Whether or not such solids are initially separated from the organic phase, extractable organic material can be separated from such solids using incineration, pyrolysis or solvent extraction techniques. It is preferred to separate as much solvent as is practicable from the solids for purposes of economics before subjecting the solids to incineration or pyrolysis.

Incineration involves incinerating the solids for an effective period of time to burn off all or substantially all of the extractable organic material intermixed with said solids.

Wet oxidation involves contacting an aqueous system with an oxidant (e.g., air, oxygen, hydrogen peroxide, nitric acid, etc.) under conditions of elevated temperature (e.g., about 300° F. to about 1000° F.) and sufficient pressure to maintain the system in liquid form or substantially liquid form (e.g., at least about 80% by weight being liquid) or as a dense supercritical fluid to convert a desired amount of the extractable organic material to carbon dioxide and water.

Pyrolysis involves heating the solids in the absence or substantial absence of an oxidant at a sufficient temperature (e.g., in excess of about 400° F.) for an effective period of time to convert the extractable organic material intermixed with such solids to a more desirable or more acceptable product. In one embodiment, the extractable organic material is converted to a product comprising carbon, methane, ethane, ethylene or a mixture of two or more thereof.

Solvent extraction involves single-step or multi-step extractions using Solvents A and/or B. These solvent extractions are sometimes referred to hereinafter as step (III) of the invention. Examples of such solvent extractions include the following:

(1) Single-step extraction using one or more of Solvent A;
(2) Single-step extraction using one or more of Solvent B;
(3) Single-step extraction using a mixture of one or more of Solvent A and one or more of Solvent B;
(4) Multi-step extraction using Solvent A followed in sequence by Solvent B;
(5) Multi-step extraction using Solvent B followed in sequence by Solvent A followed in sequence by Solvent B;
(6) Multi-step extraction using one or more mixtures of Solvents A and B followed in sequence by Solvent B;
(7) Multi-step extraction using Solvent A followed in sequence by one or more mixtures of Solvents A and B followed in sequence by Solvent B;
(8) Multi-step extraction using Solvent B followed in sequence by one or more mixtures of Solvents A and B followed in sequence by Solvent B;
(9) Multi-step extraction using a mixture of Solvents A and B followed in sequence by one or more additional mixtures of Solvents A and B; or
(10) Multi-step extraction using a mixture of Solvents A and B followed in sequence by one or more additional mixtures of Solvents A and B, followed in sequence by Solvent B.

In one embodiment of the invention, a solvent mixture is used during step (III) and the composition of the solvent mixture is optimized by using only the minimum amount of the more expensive of the solvents in the solvent mixture to provide a solubility parameter that sufficiently matches the solubility parameter of the extractable organic material to provide a sufficient extraction for the intended purpose. From an economics perspective, it may be preferable to use a solvent or solvent mixture that does not provide the most effective extraction, but provides a degree of extraction that is sufficient for the intended purpose and uses a solvent or solvent mixture that is less costly. For example, if it was determined that a solvent or solvent mixture having a single parameter solubility parameter of 8 (cal./ml.)$^{\frac{1}{2}}$ would be the most effective solvent or solvent mixture, but a less costly solvent or solvent mixture having a single parameter solubility parameter of 7 (cal./ml.)$^{\frac{1}{2}}$ was sufficient for the intended purpose, the latter might be preferred. Similarly, during steps (I) and/or (II) of the inventive process it may be preferable to use a co-solvent or co-solvent mixture, or solvent or solvent mixture that does not provide the highest degree of solubility with respect to the extractable organic material that is to be separated, but does provide a degree of solubility that is sufficient for the intended purpose.

In an optional step, the solids to be treated using solvent extraction can be mixed with one or more filter aids to facilitate the formation of a fluidpermeable mass or bed of solids. The filter aids that are useful are preferably selected from those materials having a structural integrity that does not degrade significantly when in contact with the organic material in the organic phase or the solvents used in the solvent extraction. These filter aids also preferably do not contain significant levels of EPA listed materials. Examples of filter aids that are useful include inorganic materials such as diatomaceous earth, vermiculite, perlite, pumice, sand, lime, gravel and the like; organic materials such as excelsior, saw dust, wood chips, straw, ground tree bark, ground corn cobs, de-oiled rice bran and the like; and synthetic polymeric materials such as porous polypropylene beads, blown plastics (especially off-specification blown plastics) and the like. Polyelectrolyte polymer flocculating agents are also useful. Mixtures of two or more of the foregoing filter aids can be used. The level of addition of filter aid to the feed composition is typically in the range of zero to about 500% by weight, preferably zero to about 200% by weight, more preferably zero to about 150% by weight, more preferably about 50% to about 100% by weight based on the weight of the solids. This optional step of mixing the solids with a filter aid can be effected in the extraction unit using conventional mixing techniques.

The extraction unit can be one or more pressurized vessels that may be operated in a batch mode, semi-batch mode or in a continuous mode. The extraction unit can be the same vessel or unit used during steps (I) and/or (II) of the inventive process. Thus, the extraction unit or vessel can be used to perform steps (I), (II) and (III) of the inventive process, or steps (I) and (III), or steps (II) and (III), or step (III) of said process. The extraction unit can be operated in a mixer-settler mode. That is, the vessel contents are mixed and allowed to settle, liquid is decanted off the top or drawn through the bed and removed from the bottom, more co-solvent or solvent is added, and then the sequence is repeated. When multiple vessels are employed, the vessels can be operated in parallel or in staggered sequence. Multiple vessels can be arranged in a cascade wherein effluent from one vessel that contains a relatively low concentration of extractable organic material can be used as the co-solvent or solvent in one or more other vessels. The configuration of the vessel is dependent upon the means of conveyance of the vessel contents to the vessel and the treated product from the vessel. For example, if the vessel contents are conveyed to the vessel in emulsion or slurry form, nozzles with ball valves or pinch valves can satisfactorily seal the vessel. If the vessel contents are conveyed by large bag or bucket, large diameter hatch closures can be used to satisfactorily provide closure of the vessel. For pneumatic conveyance of the treated product solids from the vessels, conventional designs including cone-shaped bottoms with manifolds of air-jet nozzles can be used. Continuous systems employing lock-hoppers or rotary valves can be used. The treated product solids can also be conveyed from the extraction vessel by slurrying the solids with water followed by an appropriate de-watering step using, for example, vacuum drum filters, clarifiers, settling tanks, centrifuges, sludge dryers and the like. The treated product solids can also be conveyed from the extractor vessel by slurrying them in a volatile solvent of, for example, from about 3 to about 5 carbon atoms (e.g., propane, butane, pentane, etc.) and then transferring the slurry to a low pressure lock hopper. The volatile solvent is thereafter separated from the solids using conventional techniques (e.g., flashing, steam stripping, etc.). The extraction vessels can employ mechanical agitators, and heating/cooling jackets as well as external thermal insulation.

The direction of flow of the solvents used in the inventive process through the solids can be upwardly, downwardly, radially, co-currently, counter-currently, or it can alternate between any of the foregoing.

The extraction unit effluent of extractable organic material and solvents can be disposed of directly (e.g., in the case wherein the feed composition being treated is a refinery waste, the effluent can be combined with an appropriate refinery stream) or the effluent can be treated to separate the extractable organic material from the solvent. The solvent can then be recycled. Separation can be accomplished by techniques known in the art including flashing and distillation.

One method for recycling the solvent involves using a pump and a heater to pump the solvents through the extraction vessel until the desired bed temperature is reached. A heated storage tank is employed to store the extraction vessel fluid effluent. A continuous flash/distillation system can be used to separate the solvents from the extracted organic materials. A cooler and separator can be used to separate water from the solvents.

If the solids are transferred from another vessel or unit to the extraction vessel, a slurry fill can be used and the excess slurry solvent can be drained down. With other filling methods, an inert gas purge can be used. With a batch or semi-batch operation the extraction vessel is typically pressurized to the desired operating pressure after the vessel is filled with the solids-containing organic phase. With a continuous or semi-continuous operation pressure within the extraction vessel is typically at the desired operating level when the solids-containing organic phase is added. In either case, however, it is to be understood that the solvent extraction can be operated at atmospheric pressure.

Solvent extraction is effected by introducing the solvent or solvent mixture into the extraction unit and mixing it with the solids for an effective period of time to extract a desired amount of the extractable organic material from said solids and this form a mixture of said extractable organic material and said solvent(s). The temperature within the extraction unit during this stage of the process is preferably in the range of about 0° F. to about 800° F., more preferably about 50° F. to about 300° F., more preferably about 150° F. to about 250° F. The pressure within the extraction unit during this stage of the process is preferably in the range of about atmospheric pressure to about 500 psig, more preferably in the range of about atmospheric pressure to about 300 psig, more preferably in the range of about atmospheric pressure to about 150 psig, more preferably about atmospheric pressure to about 100 psig, more preferably about atmospheric pressure to about 50 psig. The average contact time between the solvent and the solids is preferably in the range of about 0.01 minute to about 100 hours, more preferably in the range of about 1 second to about 8 hours, more preferably in the range of about 1 second to about 1 hour. The temperature and pressure are set at levels so that preferably at least about 30% by weight, more preferably at least about 50% by weight, more preferably at least about 70% by weight, more preferably at least about 90% by weight of the solvent or solvent mixture is in a condensed state. During this step of the process, mechanical means are preferably employed to agitate the mixture of solids and solvents. Conventional techniques such as the use of static or non-static mixers, simple mixers, and recirculating pumps can be used. Separation of the mixture of extractable organic material and solvent from the solids is preferably effected using mechanical separation means such as filtration, centrifugation, hydrocycloning or settling.

The solvent extraction can be repeated until desired levels of extraction have been achieved. With subsequent extractions the same or different solvent or mixture of solvents can be used, and the same or different operating parameters (e.g., temperature, pressure, etc.) can be used.

At the end of step (III), any solvent remaining intermixed with the solids can be separated using conventional techniques (e.g., steam stripping, flashing, drying, etc.). Because of its relatively high volatility, Solvent B is typically removed from the product solids relatively easily using such techniques. If Solvent A is used in combination with Solvent B, preferably most or all of Solvent A is removed with Solvent B. In some instances, some of Solvent A may remain intermixed with the product solids. If unacceptable levels of Solvent A remain intermixed with the product solids, a supplementary organic solvent can be used to extract such Solvent A. This additional extraction can be conducted in the extraction unit. The supplementary organic solvent can be one or more of any of the Solvents B discussed above. The temperature within the extraction unit during this step of the process is preferably in the range of about 0° F. to about 500° F., more preferably about 0° F. to about 300° F., more preferably about 0° F. to about 150° F. The pressure within the extraction unit during this step of the process is preferably in the range of atmospheric pressure to about 1000 psig, more preferably in the range of atmospheric pressure to about 500 psig, more preferably in the range of atmospheric pressure to about 300 psig. The average contact time between the supplementary organic solvent and the treated product solids is preferably in the range of about 0.01 minute to about 100 hours, more preferably about 1 second to about 8 hours, more preferably about 1 second to about 1 hour. The temperature, pressure and flow rate of the supplementary organic solvent are set at levels so that preferably at least about 30% by weight, more preferably at least about 50% by weight, more preferably at least about 70% by weight, more preferably at least about 90% by weight of the solvent is in a condensed state. When in such a condensed state, this supplementary organic solvent preferably has a density in excess of about 15 pounds per cubic foot, more preferably in excess of about 20 pounds per cubic foot, more preferably in excess of about 25 pounds per cubic foot. When the supplementary organic solvent is propane, the upper limit is preferably about 33 pounds per cubic foot. When the supplementary organic solvent is butane, the upper limit is preferably in the range of about 35 to about 40 pounds per cubic foot. The flow of the supplementary organic solvent through the solids is continued until a desired amount of Solvent A is extracted from the solids. During this step of the process, mechanical means are preferably employed to agitate the mixture of solids and solvent. Conventional techniques such as the use of non-static mixers, simple mixers, and recirculating pumps can be used. The mixture of Solvent A and supplementary organic solvent can be separated from the solids using conventional techniques such as filtration, steam stripping, etc. This mixture can be separated by displacement with water or an inert gas or by draining the solution from the extraction unit prior to depressurizing it. This step of process is conducted until all of Solvent A is extracted from the solids, or until the concentration of Solvent A remaining intermixed with the solids is reduced to an acceptable level. If the level of Solvent A intermixed with the solids is not reduced to an acceptable level, subsequent repetitions of this step can be conducted. With such subsequent extractions, the same or different supplementary organic solvent can be used, and the same or different operating parameters (e.g., temperature, pressure, flow rate, etc.) can be used. Any supplementary organic solvent remaining intermixed with the solids can be separated therefrom using conventional procedures (e.g., steam stripping, flashing, drying, etc.). The solids are then removed from the extraction unit.

In one embodiment of the invention, the solids to be treated using solvent extraction are intermixed in a solids-containing composition with extractable organic material and water, and the following process steps are conducted prior to the solvent-extraction step (III). The solids-containing composition is optionally mixed with an auxiliary organic solvent, and then heated to a sufficiently high temperature to vaporize at least part of water that is intermixed therewith. The vaporized water is separated from the solids-containing composition. The amount of auxiliary organic solvent, if any, that is added is dependent upon the characteristics of the solids-containing composition being treated, it being preferred that the solids-containing composition or mixture of solids and auxiliary organic solvent have a sufficiently low viscosity during heating so that excessive bumping or foaming does not occur. In one embodiment of the invention, the weight ratio of auxiliary organic solvent to solids-containing composition is in the range of up to about 10:1, more preferably up to about 5:1, more preferably up to about 2:1, more preferably about 1:1. The auxiliary organic solvent preferably is Solvent A. This procedure is particularly useful when the solids-containing composition contains free water. In this regard, a solids-containing composition having a free-water content in excess of about 5%, 10%, 20% or greater can be treated in accordance with this procedure. When this process step is used it is preferred to separate out at least about 20%, more preferably at least about 50%, more preferably at least about 90%, more preferably all or substantially all of the free water in the solids-containing composition being treated; optionally, part or all of the remaining water (i.e., not free water) remaining in such solids-containing composition can also be separated out. It is preferable that the auxiliary organic solvent has an initial boiling point above the boiling point of water, although solvents can be used wherein at least about 50% by weight, more preferably at least about 70% by weight, more preferably at least about 90% by weight of such solvent, boil at a temperature in excess of the boiling point of water. Heat may be supplied directly through steam coils or by the introduction of live steam into the mixture. Heat may also be supplied through external heating of the solvent or by recycling the solvent through a heat exchanger. Alternative methods of dehydration such as direct steaming, hot-air drying, etc., can be used. During and/or after vaporization of the water, the mixture that forms by the dissolution of extracted organic material in the auxiliary organic solvent can be removed from the solids using conventional mechanical separation techniques such as decanting, settling, filtration, centrifugation, etc.

In one embodiment of the invention, the solvent extraction step (III) is conducted until part but not all of the extractable organic material has been separated from the solids. The remaining solids, which contain some extractable organic material intermixed therewith, are then subjected to incineration, pyrolysis or wet oxidation for the purpose of separating the remaining extractable organic material from the solids, or reducing the contents of such extractable organic material to desired levels.

In the event undesirable metals or metal compounds (e.g., EPA listed metals such as nickel, chromium, and the like) are intermixed with the solids, such solids can be treated with one or more fixation chemicals to immobilize the metal or metal compound sufficiently to thereby prevent or reduce to acceptable levels subsequent leaching of the metal or metal compound from the solids. This can be done when the solids are dispersed in the emulsion phase during or at the end of step (II) of the inventive process, or when the solids are dispersed in the organic-rich phase and/or water-rich phase after the emulsion is broken. This procedure can also be conducted after the solids have undergone post-treatment using solvent extraction, incineration, wet oxidation or pyrolysis as discussed above. The solids can be treated with one or more fixation chemicals by mixing the solids with the fixation chemical in water at ambient temperatures. The resulting slurry can then be de-watered using conventional techniques (e.g., filtration, centrifugation, settling, etc.). Various fixation chemicals that are commercially available are useful with the inventive process. Examples of such useful fixation chemicals include commercially available silica- or silicate-bearing solutions, fly ash and sodium sulfide. Pozzalime, a product of Mineral By-Products, Inc., identified as containing about 60% CaO and 16% $SiO_2$, is a commercially available fixation chemical that is useful. The fixation chemical is typically blended with the solids at levels of up to about 100% by weight based on the weight of said solids, preferably from about 10 to about 50% by weight based on the weight of said solids.

The inventive process can be conducted on a batch, semi-batch or continuous basis. The term "semi-batch" refers to embodiments wherein parts of the process, e.g., step (I), are conducted on a batch basis, while other parts, e.g., step (II), are conducted on a continuous basis.

Figure 2:
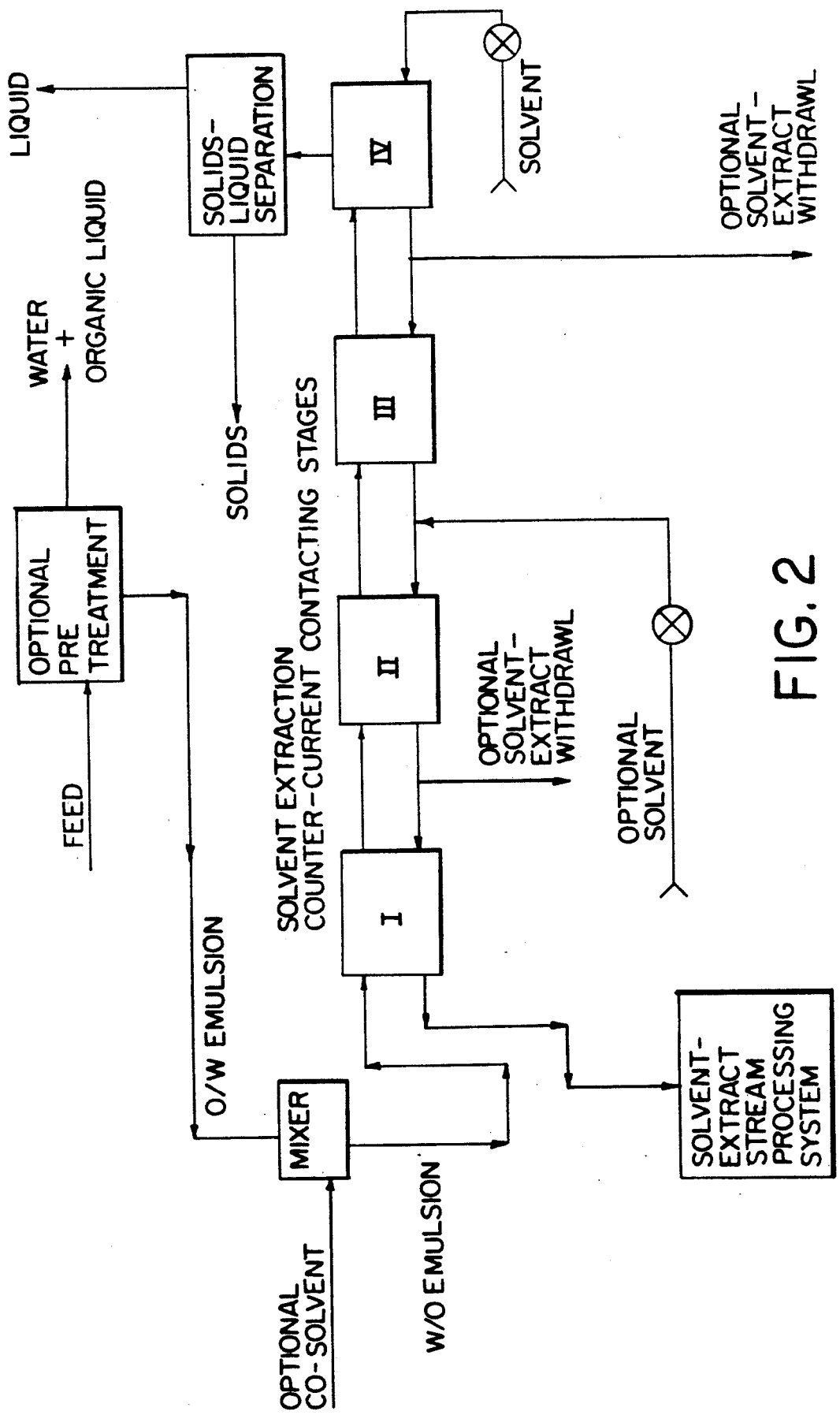
FIG. 2 is a flow sheet illustrating another embodiment of the invention wherein a counter-current process is used to separate extractable organic material from a feed composition comprising an oil-in-water emulsion comprising a continuous aqueous phase, a discontinuous organic phase comprising said extractable organic material, and solids dispersed in said emulsion.
Figure 3:
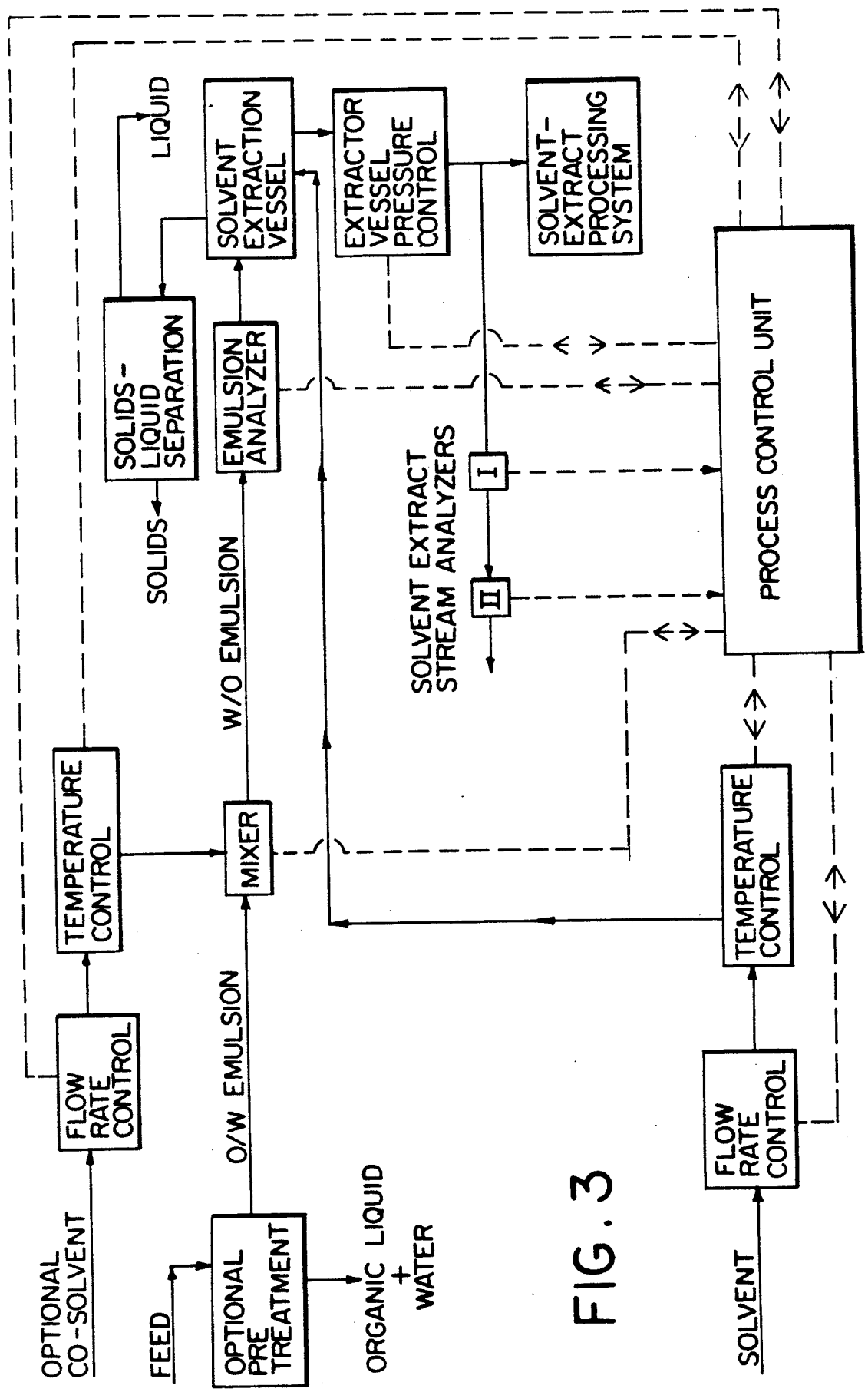
FIG. 3 is a flow sheet illustrating another embodiment of the invention wherein a control system is used in a process to separate extractable organic material from a feed composition comprising an oil-in-water emulsion comprising a continuous aqueous phase, a discontinuous organic phase comprising said extractable organic material, and solids dispersed in said emulsion.

In order to further describe the inventive process, reference is made to FIGS. 1-3 wherein various illustrated embodiments of the inventive process are disclosed. Any of the feed compositions discussed above can be treated with each of the illustrated embodiments. The co-solvents, solvents, operating parameters and procedures, and apparatus discussed above are applicable to these illustrated embodiments.

FIG. 1 is a flow sheet illustrating a batch or continuous process for separating extractable organic material from a feed composition comprising an oil-in-water emulsion containing dispersed solids. The process uses an optional pretreatment system, mixer for inverting the emulsion, solvent extraction unit for extracting extractable organic material from the emulsion, a solids-liquid separation unit, and a solvent-extract processing system. The feed composition is conveyed to the optional pretreatment system wherein part of the water and organic liquid (e.g., oil) is optionally separated out from the feed composition. The feed composition (whether or not pretreated) is conveyed to a mixer wherein vigorous batch, semi-batch or in-line continuous mixing is used to invert the emulsion to a solids-containing water-in-oil emulsion. One or more optional co-solvents can be added during this emulsion inversion step. The co-solvent can be Solvent A, Solvent B, or a mixture thereof. The inverted solids-containing water-in-oil emulsion is then conveyed to the solvent extraction unit. The extraction unit has a solvent inlet and an extract outlet and is preferably equipped with agitation means (e.g., non-static mixer, simple mixer, recirculating pump, etc.) to mix the vessel contents. Agitation is optional, but preferable, and when used can be used on a continuous or intermittent basis. One or more of Solvent B is added to the extraction unit in contact with the solids-containing water-in-oil emulsion. Contact between the solvent and the solids-containing water-in-oil emulsion is maintained for an effective amount of time to permit: formation of a system comprising at least two phases, one of the phases being an emulsion phase comprising the solids-containing water-in-oil emulsion, the other phase being a solvent phase; and replacement of at least some of the extractable organic material in the emulsion phase with solvent from the solvent phase. The replaced extractable organic material disperses or dissolves in the solvent phase. The solvent phase is separated from the extractor using conventional techniques (e.g., drainage from the bottom, decantation, extraction using a volatile solvent, etc.). The emulsion in the emulsion phase can then be broken to provide separate water-rich and organic-rich phases. This is done by separating an effective amount of organic solvent from the separated emulsion phase to cause separation of the separated emulsion phase into an organic-rich phase and a water-rich phase. This is preferably accomplished by flashing or vaporizing the solvent in the emulsion using known techniques. The organic-rich phase is then separated from the water-rich phase using conventional techniques (e.g., decantation, centrifugation, extraction using a volatile solvent, etc.). The solids that are hydrophilic will generally be dispersed in the aqueous phase. The water-rich phase is advanced to the solids-liquid separation unit wherein the solids are separated using conventional solids-water separation techniques (e.g., filtration, centrifugation, vaporization, etc.). These solids can contain extractable organic material intermixed therewith which can be removed using incineration, pyrolysis, wet oxidation or solvent extraction as discussed above. If solvent extraction is used, the solids can be returned to the extraction unit. The solids that are hydrophobic will generally be dispersed in the organic-rich phase. These solids may contain extractable organic material intermixed therewith which can be separated using solvent extraction, incineration or pyrolysis as discussed above. If solvent extraction is used, the solvent or solvent mixture used in the extraction can be the same as the co-solvent or co-solvent mixture used during step (I) and/or the same as the solvent or solvent mixture used during step (II). The solvent can be, for example, a mixture of Solvent A and Solvent B and the extraction procedure can be a one-step extraction; Solvent A followed by Solvent B in a two-step extraction; or Solvent B followed by Solvent A and then followed by Solvent B in a three-step extraction. Other combinations and extraction sequences can be used as discussed above. The flow of solvent through the solids dissolves the extractable organic materials that are intermixed with the solids and displaces the resulting mixture to and through the extract outlet. The solvent-extract effluent which comprises a mixture of separated extracted organic material and solvent, is advanced to the solvent-extract processing system wherein it is disposed of using conventional procedures or, for example, in the treatment of a refinery waste, returned to an appropriate location in the refinery system (e.g., the crude tower) for further processing. If the concentration level of extractable organic material in the solvent-extract effluent is relatively low, the effluent can optionally be recycled. Solvent is continually circulated through the extraction vessel and solvent-extract is continually removed until all or substantially all of the extracted organic materials intermixed with the solids are removed, or their concentration is reduced to acceptable levels. The resulting treated product remaining in the extraction unit comprises the solids intermixed with solvent. The solvent remaining intermixed with the solids is separated from the solids by any of a number of conventional techniques including displacing the solvent with water or an inert gas, drying the solids, etc. If the concentration of Solvent A remaining intermixed with the solids is at an unacceptably high level, Solvent B can be circulated through the solids until a sufficient quantity of Solvent A is removed. Any Solvent B remaining intermixed with the solids can be separated from such solids using conventional techniques including displacement with water or an inert gas, drying the solids, etc. If the solids contain undersirable levels of extractable organic material intermixed therewith, the solids can be subjected to further solvent extraction steps or they can be subjected to incineration, pyrolysis or wet oxidation to reduce the content of extractable organic material to desired levels. If the solids contain undesirable levels of metals and/or metal compounds, the solids can be subjected to metal fixation. The solids are then disposed of using conventional solids disposal techniques (e.g., landfill, etc.).

FIG. 2 is a flow sheet illustrating a counter-current process for separating extractable organic material from an oil-in-water emulsion containing dispersed solids. The process uses an optional pretreatment system, mixer for inverting the emulsion, counter-current solvent extraction unit for extracting extractable organic material from the emulsion, and a solvent-extract processing system. The feed composition is optionally conveyed to the optional pretreatment system wherein part of the water and organic liquid (e.g., oil) is separated out from the feed composition. The feed composition (whether or not pretreatable) is conveyed to a mixer wherein vigorous in-line continuous mixing is used to invert the emulsion to a solids-containing water-in-oil emulsion. One or more optional co-solvents or co-solvent mixtures can be added during this emulsion inversion step. The co-solvent or co-solvent mixture can be Solvent A, Solvent B, or a mixture thereof. The inverted solids-containing water-in-oil emulsion is then conveyed to the solvent extraction unit. The solvent extraction unit consists of a series of four stages of interconnected mixer-settlers, labeled I-IV in FIG. 2. (It is to be understood that less than four or more than four mixer-settlers can be used depending upon the particular requirements for the desired extraction.) The solids-containing water-in-oil emulsion is advanced to stage I wherein it is contacted with solvent-extract from stage II. The contents of the mixer-settler in stage I are mixed for an effective period of time to permit: formation of a system comprising at least two phases, one of the phases being an emulsion phase comprising the solids-containing water-in-oil emulsion, the other phase being a solvent phase comprising the solvent-extract from stage II; and replacement of at least part of the extractable organic material with part of the solvent, the replaced extractable organic material being dispersed or dissolved in the solvent phase. The solvent phase is removed from stage I and advanced to the solvent-extract stream processing system. The solids-containing emulsion phase in stage I is conveyed from stage I to stage II. In stage II, the emulsion is mixed with solvent-extract from stage III and optionally fresh solvent (i.e., Solvent B) for an effective period of time to effect replacement of additional extractable organic material in the emulsion with the solvent in stage II. The displaced extractable organic material disperses or dissolves in the solvent. Solvent-extract from stage II is advanced to stage I. The solids-containing emulsion in stage II is conveyed to stage III. In stage III, the emulsion is mixed with solvent-extract from stage IV for an effective period of time to effect replacement of additional extractable organic material in the emulsion with the solvent in stage III. The displaced extractable organic material disperses or dissolves in the solvent. The solvent-extract from stage III is advanced to stage II. The solids-containing emulsion in stage III is conveyed to stage IV. The emulsion in stage IV is mixed with solvent (i.e., Solvent B) for an effective period of time to effect replacement of additional extractable organic in the emulsion with the solvent in stage IV. The displaced extractable organic material disperses or dissolves in the solvent. Solvent-extract from stage IV is advanced to stage III. Optionally, part of the solvent-extract from stages II and/or IV can be withdrawn from the system. The solids-containing emulsion in stage IV is conveyed to a solids-liquid separator wherein the emulsion is broken and the solids are separated from the solvent and water in said emulsion. This is done by separating an effective amount of organic solvent from the separated emulsion phase to cause separation of the separated emulsion phase into an organic-rich phase and a water-rich phase. This is preferably accomplished by flashing or vaporizing the solvent using known techniques. The organic-rich phase is then separated from the water-rich phase using conventional techniques (e.g., decantation, centrifugation, extraction using a volatile solvent, etc.). The solids that are hydrophilic will generally be dispersed in the water-rich phase and can be separated therefrom using conventional solids-water separation techniques (e.g., filtration, centrifugation, vaporization, etc.). The solids that are hydrophobic will generally be dispersed in the organic-rich phase. These solids can be separated from the organic-rich phase using any of the solvent extraction procedures discussed above. The solvent-extract effluent from stage I, which comprises a mixture of extracted organic material and solvent, is advanced to the solvent extract processing system wherein it is disposed of using conventional procedures or, for example, in the treatment of a refinery waste, returned to a appropriate location in the refinery system for further processing.

FIG. 3 is a flow sheet illustrating a process similar to the process illustrated in FIG. 1 with the exception that a control system is provided. The pretreatment system, mixer for inverting the emulsion, solvent extraction vessel, solvent-extract processing system and solids disposal techniques described above with respect to FIG. 1 are applicable to the system illustrated in FIG. 3. The process illustrated in FIG. 3 also includes flow rate and temperature control systems for the solvents and the co-solvents, an extractor vessel pressure control system, an emulsion analyzer, and solvent extract stream analyzers. The process also includes a process control unit for monitoring and controlling each of the foregoing systems. The flow rate control systems for the solvents and co-solvents are entirely conventional. An example of such a flow rate control system would include a mass flow meter for measuring flow-rate in combination with a pump or remotely actuated valve for controlling flow rate. The temperature control systems are also entirely conventional. An example of such a temperature control system would include a thermocouple for measuring temperature in combination with a heating element or heat exchanger for changing the temperature. The extractor vessel pressure control is also entirely conventional. An example of such a pressure control system would include a back-pressure regulator. The solvent extract stream analyzers I and II are entirely conventional. An example of analyzer I would be a diode array spectrophotometer which monitors transmission of light at multiple wave lengths through a transparent flow cell through which the solvent-extract stream flows. An example of analyzer II would be a fluorometer which monitors fluorescence of the solvent-extract stream excited by UV irradiation while flowing through a transparent fluorescence cell. The emulsion analyzer analyzes the emulsion and determines whether inversion has been effected. An example of such an analyzer would be a conductivity measuring device. The process control unit receives output from the analyzers I and II and communicates with the flow rate control systems for the solvents and co-solvents to provide an appropriate flow of such materials. The information from analyzers I and II is also used to control the inlet temperature for the solvents and co-solvents and the pressure of the solvent extraction vessel. The information from the emulsion analyzer is used to control the amount of mixing in the phase inversion mixer and the amount of co-solvent addition to said mixer. The process control unit can be a microprocessor or a computer. The pathways providing for the flow of communication between the flow rate control systems, temperature control systems, emulsion analyzer, pressure control system and analyzers I and II to and from the process control unit can be comprised of wires carrying analog or digital electrical signals, fiber optics carrying light signals, or tubing carrying hydraulic or pneumatic signals. The process control unit can be replaced by human operators reading displays and adjusting manual controls. A combination of the foregoing can be used.

The following examples are illustrative of the inventive process. Unless otherwise indicated, in the following examples as well as throughout the entire specification and in the appended claims, all parts and percentages are by weight, and all temperatures are in degrees Fahrenheit.

EXAMPLE 1

The feed composition is a solids-stabilized, oil-in-water emulsion having a water content of 15.5% by weight, an oil content of 81.1% by weight, and a solids content of 3.4% by weight. 100 parts by weight of the feed composition and 100 parts by weight of toluene are mixed under high-shear conditions in a Waring blender for 15 seconds. The resulting water-in-oil emulsion is placed in an extraction vessel equipped with a solvent inlet and an effluent outlet. Extraction is effected using 200 parts by weight of propane at a temperature of 75° F. and a pressure of 125 psig. 291 parts by weight of organic effluent is removed, the effluent constituting essentially all of the added toluene and more than 90% of the oil from the original feed composition.

EXAMPLE 2

100 parts by weight of the feed composition used in Example 1 and 78 parts by weight of coker kerosine are mixed under high-shear conditions in a Waring blender for 3 minutes. The resulting water-in-oil emulsion is placed in an extraction vessel equipped with a solvent inlet and an effluent outlet. Extraction is effected using 200 parts by weight of liquid propane. 293 parts by weight of organic effluent is removed, the effluent constituting 100% by weight of the added kerosine and more than 97% of the oil from the original feed composition.

EXAMPLE 3

100 parts by weight of the feed composition used in Example 1 and 66 parts by weight of pentane are mixed under high-shear conditions in a Waring blender for 3 minutes. The resulting water-in-oil emulsion is placed in an extraction vessel equipped with a solvent inlet and an effluent outlet. Extraction is effected using 100 parts by weight of liquid propane. Analysis of the extractor bottoms indicates a 95% by weight recovery of oil from the feed composition.

An advantage of this invention is that an efficient, economical and reliable process is provided for extracting organic materials (e.g., oil) and optionally hazardous organic materials from solids-stabilized oil-in-water emulsions. For those emulsions containing hazardous materials, the product solids are rendered suitable for land disposal and/or subsequent facilitated handling and treatment. An advantage of this invention is that fine particulate solids (e.g., solids with average diameters of about 50 microns or less) can be treated using solvent extraction at solvent velocities that would normally entrain the solids but do not because of the presence of water.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

We claim:

1. A process for separating extractable organic material from a feed composition comprising an oil-in-water emulsion comprising a continuous aqueous phase, a discontinuous organic liquid phase comprising said extractable organic material, and solids dispersed in said emulsion, the process comprising the steps of:
    (I) subjecting said feed composition to sufficient shear to convert said feed composition to a water-in-oil emulsion; and
    (II) contacting said water-in-oil emulsion with at least one organic solvent, said organic solvent being capable of forming with said emulsion a system comprising at least two phases and being capable of dissolving at least about ten parts of said extractable organic material per million parts of said organic solvent at the temperature wherein at least about 50% by weight of said solvent boils at atmospheric pressure; forming a system comprising at least two phases, one of said phases being an emulsion phase comprising said emulsion and the other of said phases being a solvent phase comprising said solvent; extracting at least part of said extractable organic material with part of said solvent, the extracted extractable organic material being dispersed in said solvent phase; and separating said emulsion phase from said solvent phase.

2. The process of claim 1 further comprising the steps of: separating an effective amount of said organic solvent from said separated emulsion phase to cause separation of said emulsion phase into an organic-rich phase and a water-rich phase; and separating said organic-rich phase from said water-rich phase.

3. The process of claim 1 wherein said solids are intermixed with at least one metal and/or metal compound, said process including contacting said solids with an effective amount of at least one fixation chemical to reduce the rate of leaching of said metal and/or metal compound from said solids.

4. The process of claim 1 wherein said mixing during step (I) is effected using vigorous batch mixing, continuous in-line mixing, or a combination thereof.

5. The process of claim 1 wherein during step (I) said feed composition is mixed with at least one co-solvent.

6. The process of claim 5 wherein said co-solvent is a solvent mixture, said solvent mixture containing at least one first organic solvent and at least one second organic solvent, said first organic solvent being capable of dissolving at least about ten parts of said extractable organic material per million parts of said first organic solvent at the temperature wherein at least about 50% by weight of said first organic solvent boils at atmospheric pressure, said second organic solvent being capable of dissolving at least about ten parts of said first organic solvent per million parts of said second organic solvent at the temperature wherein at least about 50% by weight of said second organic solvent boils at atmospheric pressure.

7. The process of claim 5 wherein said co-solvent is selected from the group consisting of at least one aromatic compound, aliphatic compound, cycloaliphatic compound, aliphatic-substituted aromatic compound, cycloaliphatic-substituted aromatic compound, aliphatic-substituted cycloaliphatic compound, or mixture of two or more thereof.

8. The process of claim 5 wherein said co-solvent is selected from the group consisting of benzene, toluene, xylene, naphthalene, kerosene, fuel oil, or a mixture of two or more thereof.

9. The process of claim 5 wherein said co-solvent is selected from the group consisting of at least a light reformate, at least one heavy reformate, or mixture thereof.

10. The process of claim 5 wherein said co-solvent is selected from the group consisting of an aliphatic, hydrocarbon of from 2 to about 9 carbon atoms, a cycloaliphatic or hydrocarbon-substituted cycloaliphatic hydrocarbon of from 3 to about 9 carbon atoms, a halohydrocarbon of from 1 to about 9 carbon atoms, or a mixture of two or more thereof.

11. The process of claim 5 wherein said co-solvent is selected from the group consisting of propane, cyclopropane, propylene, n-butane, isobutane, cyclobutane, butene, butadiene, isobutylene, n-pentane, isopentane, neopentane, cyclopentane, pentene, cyclopentene, pentadiene, cyclopentadiene, cyclohexane, cyclohexene, cyclohexadiene, methylene chloride, dichlorodifluoromethane, trichlorofluoromethane, chloroethane, trichloroethane, dichlorotetrafluoroethane, trichloroethylene, tetrafluoroethylene, chloropropane, cyclohexane, cyclohexene, cyclohexadiene, methylene chloride, dichlorodifluoromethane, trichlorofluoromethane, chloroethane, trichloroethane, dichlorotetrafluoroethane, trichloroethylene, tetrafluoroethylene, chloropropane, chlorobutane, chloropentane, dichloropentane, or a mixture of two or more thereof.

12. The process of claim 5 wherein said co-solvent is selected from the group consisting of liquified petroleum gas, gas well condensate, straight run distillate, process-generated distillate, coker distillate, or a mixture of two or more thereof.

13. The process of claim 2 wherein said organic solvent comprises at least one first organic solvent and the solids in said separated organic-rich phase and/or said separated water-rich phase are intermixed with at least part of said extractable organic material, said process comprising the additional steps of:

contacting said solids with at least one second organic solvent, said second organic solvent being the same or different than said first organic solvent and being capable of dissolving at least about ten parts of said extractable organic material per million parts of said second organic solvent at the temperature wherein at least about 50% by weight of said second organic solvent boils at atmospheric pressure; dissolving at least part of said extractable organic material in said second organic solvent to form a solvent-extract mixture; and separating at least part of said solvent-extract mixture from said solids.

14. The process of claim 2 wherein said solvent comprises at least one first organic solvent and the solids in said separated organic-rich phase and/or said separated water-rich phase are intermixed with at least part of said extractable organic material, said process comprising the additional steps of:

contacting said solids with at least one second organic solvent, said second organic solvent being the same or different than said first organic solvent and being capable of dissolving at least about ten parts of said extractable organic material per million parts of said second organic solvent at the temperature wherein at least about 50% by weight of said second organic solvent boils at atmospheric pressure; dissolving at least part of said extractable organic material in said second organic solvent to form a solvent-extract mixture; and separating at least part of said solvent-extract mixture from said solids to provide an intermediate composition, said intermediate composition comprising said solids and at least part of second organic solvent; and contacting said intermediate composition with at least one third organic solvent, said third organic solvent being more volatile than said second organic solvent and being capable of dissolving at least about ten parts of said second organic solvent per million parts of said third organic solvent at the temperature wherein at least about 50% by weight of said third organic solvent boils at atmospheric pressure; dissolving at least part of said second organic solvent in said third organic solvent to form a solvent-solvent mixture; and separating said solvent-solvent mixture from said intermediate composition.

15. The process of claim 2 wherein said solvent comprises at least one first organic solvent and the solids in said separated organic-rich phase and/or said separated water-rich phase are intermixed with at least part of said extractable organic material, said process comprising the additional steps of:

contacting said solids with at least one solvent mixture, said solvent mixture comprising at least one second organic solvent and at least one third organic solvent, said first organic solvent being the same or different than said second or said third organic solvent, said second organic solvent being capable of dissolving at least about ten parts of said extractable organic material per million parts of said second organic solvent at the temperature wherein at least about 50% by weight of said second organic solvent boils at atmospheric pressure, said third organic solvent being more volatile than said second organic solvent and being capable of dissolving at least about ten parts of said second organic solvent per million parts of said third organic solvent at the temperature wherein at least about 50% by weight of said third organic solvent boils at atmospheric pressure; dissolving at least part of said extractable organic material in said solvent mixture to form a solvent-extract mixture; and separating at least part of said solvent-extract mixture from said solids to provide a treated composition.

16. The process of claim 15 wherein said treated composition comprises solids and at least part of said second organic solvent, said process including the additional steps of:

contacting siad treated composition with at least one supplementary organic solvent, dissolving at least part of said second organic solvent in said supplementary organic solvent to form a supplementary solvent-solvent mixture, and separating said supplementary solvent-solvent mixture from said treated composition, said supplementary organic solvent being more volatile than said second organic solvent and being capable of dissolving at least about ten parts of said second organic solvent per million parts of said supplementary organic solvent at the temperature wherein at least about 50% by weight of said supplementary organic solvent boils at atmospheric pressure.

17. The process of claim 2 wherein the solids in said separated organic-rich phase and/or said separated water-rich phase are intermixed with at least part of said extractable organic material, said process including the additional step of incinerating said solids for an effective period of time to burn off a desired amount of said extractable organic material from said solids.

18. The process of claim 2 wherein the solids in said separated organic-rich phase and/or said separated water-rich phase are intermixed with at least part of said extractable organic material, said process including the additional step of heating said solids in the absence or substantial absence of an oxidant for an effective period of time and at a sufficient temperature to convert said extractable organic material to a product comprising carbon, methane, ethane, ethylene, or a mixture of two or more thereof.

19. The process of claim 2 wherein the solids in said separated water-rich phase are in an intermediate composition comprising solids, water, and at least part of said extractable organic material, said process including the additional step of contacting said intermediate composition with an oxidant at a temperature of about 300° F. to about 1000° F. and a pressure sufficient to maintain said intermediate composition in a liquid or substantially liquid form or in the form of a dense supercritical fluid for an effective period of time to convert a desired amount of said extractable organic material to carbon dioxide and water.

20. The process of claim 2 wherein said separated organic-rich phase comprises water, said process comprising the additional steps of heating said separated organic-rich phase at a sufficient temperature for an effective period of time to vaporize at least part of the water in said separated organic-rich phase, and separating said vaporized water from said separated organic-rich phase.

21. The process of claim 2 wherein said separated organic-rich phase comprises water, said process comprising the additional steps of mixing at least part of said separated organic-rich phase with an auxiliary organic solvent, vaporizing at least part of the water in said separated organic-rich phase, and separating said vaporized water from said separated organic-rich phase, the boiling point of at least about 50% by weight of said auxiliary organic solvent being in excess of the boiling point of water, said auxiliary organic solvent being capable of dissolving at least about ten parts of said extractable organic material per million parts of said auxiliary organic solvent at the temperature wherein at least about 50% by weight of said auxiliary organic solvent boils at atmospheric pressure.

22. The process of claim 1 with the step of separating at least part of said water and/or at least part of said organic liquid from said feed composition prior to step (I).

23. The process of claim 1 with the step of recycling at least part of said separated solvent phase into contact with said emulsion phase.

24. The process of claim 1 wherein said feed composition comprises:
(i) from about 10% to about 90% by weight water;
(ii) from about 10% to about 90% by weight organic liquid;
(iii) from about 0.01% to about 50% by weight solids;
(iv) up to about 10% by weight metals and/or metal compounds; and
(v) up to about 50% by weight hazardous organic material.

25. The process of claim 1 wherein said organic solvent is selected from the group consisting of an aliphatic hydrocarbon of from 2 to about 9 carbon atoms, a cycloaliphatic or hydrocarbon-substituted cycloaliphatic hydrocarbon compound of 3 to about 9 carbon atoms, or a halohydrocarbon of from 1 to about 9 carbon atoms, or a mixture of two or two or more thereof.

26. The process of claim 1 wherein said organic solvent is selected from the group consisting of propane, cyclopropane, propylene, n-butane, isobutane, cyclobutane, butene, butadiene, isobutylene, n-pentane, isopentane, neopentane, cyclopentane, pentene, cyclopentene, pentadiene, cyclopentadiene, cyclohexane, cyclohexene, cyclohexadiene, methylene chloride, dichlorodifluoromethane, trichlorofluoromethane, chloroethane, trichloroethane, dichlorotetrafluoroethane, trichloroethylene, tetrafluoroethylene, chloropropane, chlorobutane, chloropentane, dichloropentane, or a mixture of two or more thereof.

27. The process of claim 1 wherein said organic solvent is propane.

28. The process of claim 1 wherein said organic solvent is selected from the group consisting of liquified petroleum gas, gas well condensate, straight run gasoline, or a mixture of two or more thereof.

29. The process of claim 1 wherein said solvent is at least one solvent mixture, said solvent mixture comprising up to about 50% by weight of at least one aromatic and/or hydrocarbon-substituted aromatic compound of up to about 12 carbon atoms.

30. The process of claim 13 wherein said second organic solvent is selected from the group consisting of at least one aromatic compound, aliphatic compound, cycloaliphatic compound, aliphatic-substituted aromatic compound, cycloaliphatic-substituted aromatic compound, aliphatic-substituted cycloaliphatic compound, or mixture of two or more thereof.

31. The process of claim 13 wherein said second organic solvent is selected from the group consisting of benzene, toluene, xylene, naphtha, kerosene, gas oil, fuel oil, or a mixture of two or more thereof.

32. The process of claim 13 wherein said second organic solvent is selected from the group consisting of at least one light reformate, at least one heavy reformate, or mixture thereof.

33. The process of claim 13 wherein said second organic solvent is selected from the group consisting of at least one straight-run distillate, at least one process-generated distillate, at least one coker distillate, or mixture of two or more thereof.

34. The process of claim 13 wherein said second organic solvent is selected from the group consisting of an aliphatic hydrocarbon of from 2 to about 9 carbon atoms, a cycloaliphatic or hydrocarbon-substituted cycloaliphatic hydrocarbon of 3 to about 9 carbon atoms, a halohydrocarbon of from 1 to about 9 carbon atoms, or a mixture of two or more thereof.

35. The process of claim 13 wherein said second organic solvent is selected from the group consisting of propane, cyclopropane, propylene, n-butane, isobutane, cyclobutane, butene, butadiene, isobutylene, n-pentane, isopentane, neopentane, cyclopentane, pentene, cyclopentene, pentadiene, cyclopentadiene, cyclohexane, cyclohexene, cyclohexadiene, methylene chloride, dichlorodifluoromethane, trichlorofluoromethane, chloroethane, trichloroethane, dichlorotetrafluoroethane, trichloroethylene, tetrafluoroethylene, chloropropane, chlorobutane, chloropentane, dichloropentane, or a mixture of two or more thereof.

36. The process of claim 13 wherein said second organic solvent is propane.

37. The process of claim 13 wherein said second organic solvent is selected from the group consisting of liquified petroleum gas, gas well condensate, straight run gasoline, or a mixture of two or more thereof.

38. The process of claim 14 wherein said second organic solvent is selected from the group consisting of at least one aromatic compound, aliphatic compound, cycloaliphatic compound, aliphatic-substituted aromatic compound, cycloaliphatic-substituted aromatic compound, aliphatic-substituted cycloaliphatic compound, or mixture of two or more thereof.

39. The process of claim 14 wherein said second organic solvent is selected from the group consisting of benzene, toluene, xylene, naphtha, kerosene, gas oil, fuel oil, or a mixture of two or more thereof.

40. The process of claim 14 wherein said second organic solvent is selected from the group consisting of at least one light reformate, at least one heavy reformate, or mixture thereof.

41. The process of claim 14 wherein said second organic solvent is selected from the group consisting of at least one straight-run distillate, at least one process-generated distillate, at least one coker distillate, or mixture thereof.

42. The process of claim 14 wherein said third organic solvent is selected from the group consisting of an aliphatic hydrocarbon of from 2 to about 9 carbon atoms, a cycloaliphatic or hydrocarbon-substituted cycloaliphatic hydrocarbon of 3 to about 9 carbon atoms, a halohydrocarbon of from 1 to about 9 carbon atoms, or a mixture of two or more thereof.

43. The process of claim 14 wherein said third organic solvent is selected from the group consisting of propane, cyclopropane, propylene, n-butane, isobutane, cyclobutane, butene, butadiene, isobutylene, n-pentane, isopentane, neopentane, cyclopentane, pentene, cyclopentene, pentadiene, cyclopentadiene, cyclohexane, cyclohexene, cyclohexadiene, methylene chloride, dichlorodifluoromethane, trichlorofluoromethane, chloroethane, trichloroethane, dichlorotetrafluoroethane, trichloroethylene, tetrafluoroethylene, chloropropane, chlorobutane, chloropentane, dichloropentane, or a mixture of two or more thereof.

44. The process of claim 14 wherein said third organic solvent is propane.

45. The process of claim 14 wherein said third organic solvent is selected from the group consisting of liquified petroleum gas, gas well condensate, or a mixture of two or more thereof.

46. The process of claim 15 wherein said second organic solvent is selected from the group consisting of at least one aromatic compound, aliphatic compound, cycloaliphatic compound, aliphatic-substituted aromatic compound, cycloaliphatic-substituted aromatic compound, aliphatic-substituted cycloaliphatic compound, or mixture of two or more thereof.

47. The process of claim 15 wherein said second organic solvent is selected from the group consisting of benzene, toluene, xylene, naphtha, kerosene, gas oil, fuel oil, or a mixture of two or more thereof.

48. The process of claim 15 wherein said second organic solvent is selected from the group consisting of at least one light reformate, at least one heavy reformate, or mixture thereof.

49. The process of claim 15 wherein said second organic solvent is selected from the group consisting of at least one straight-run distillate, at least one process-generated distillate, at least one coker distillate, or mixture of two or more thereof.

50. The process of claim 15 wherein said third organic solvent is selected from the group consisting of an aliphatic hydrocarbon of from 2 to about 9 carbon atoms, a cycloaliphatic or hydrocarbon-substituted cycloaliphatic hydrocarbon of 3 to about 9 carbon atoms, a halohydrocarbon of from 1 to about 9 carbon atoms, or a mixture of two or more thereof.

51. The process of claim 15 wherein said third organic solvent is selected from the group consisting of propane, cyclopropane, propylene, n-butane, isobutane, cyclobutane, butene, butadiene, isobutylene, n-pentane, isopentane, neopentane, cyclopentane, pentene, cyclopentene, pentadiene, cyclopentadiene, cyclohexane, cyclohexene, cyclohexadiene, methylene chloride, dichlorodifluoromethane, trichlorofluoromethane, chloroethane, trichloroethane, dichlorotetrafluoroethane, trichloroethylene, tetrafluoroethylene, chloropropane, chlorobutane, chloropentane, dichloropentane, or a mixture of two or more thereof.

52. The process of claim 15 wherein said third organic solvent is propane.

53. The process of claim 15 wherein said third organic solvent is selected from the group consisting of liquified petroleum gas, gas well condensate, straight run gasoline, or a mixture of two or more thereof.

54. The process of claim 16 wherein said supplementary organic solvent is selected from the group consisting of an aliphatic hydrocarbon of from 2 to about 9 carbon atoms, a cycloaliphatic or hydrocarbon-substituted cycloaliphatic hydrocarbon of 3 to about 9 carbon atoms, a halohydrocarbon of from 1 to about 9 carbon atoms, or a mixture of two or more thereof.

55. The process of claim 16 wherein said supplementary organic solvent is selected from the group consisting of propane, cyclopropane, propylene, n-butane, isobutane, cyclobutane, butene, butadiene, isobutylene, n-pentane, isopentane, neopentane, cyclopentane, pentene, cyclopentene, pentadiene, cyclopentadiene, cyclohexane, cyclohexene, cyclohexadiene, methylene chloride, dichlorodifluoromethane, trichlorofluoromethane, chloroethane, trichloroethane, dichlorotetrafluoroethane, trichloroethylene, tetrafluoroethylene, chloropropane, chlorobutane, chloropentane, dichloropentane, or a mixture of two or more thereof.

56. The process of claim 16 wherein said supplementary organic solvent is propane.

57. The process of claim 16 wherein said supplementary organic solvent is selected from the group consisting of liquified petroleum gas, gas well condensate, straight run gasoline, or a mixture of two or more thereof.

58. The process of claim 1 wherein said process is operated on a batch or semi-batch basis.

59. The process of claim 1 wherein said process is operated on a continuous basis.

60. A process for separating extractable organic material from a feed composition comprising an oil-in-water emulsion comprising a continuous aqueous phase, a discontinuous organic phase comprising said extractable organic material, solids dispersed in said emulsion, and one or more metals and/or metal compounds dispersed in said emulsion, the process comprising the steps of:

subjecting said feed composition to sufficient shear to convert said feed composition to a water-in-oil emulsion;

contacting said water-in-oil emulsion with at least one organic solvent, said solvent being capable of forming a two-phase system with said emulsion and being capable of dissolving at least about ten parts of said extractable organic material per million parts of said organic solvent at the temperature wherein at least about 50% by weight of said organic solvent boils at atmospheric pressure;

forming a two-phase system, one of said phases being an emulsion phase comprising said emulsion and the other of said phases being a solvent phase comprising said solvent;

extracting at least part of said extractable organic material with part of said solvent, the extracted extractable organic material being dispersed in said solvent phase;

separating said emulsion phase from said solvent phase;

separating an effective amount of said organic solvent from said separated emulsion phase to cause separation of said separated emulsion phase into an organic-rich phase and a water-rich phase;

separating said organic-rich phase from said water-rich phase, said separated organic-rich phase and/or said separated water-rich phase comprising at least part of said solids and at least part of said metals and/or metal compounds;

contacting said solids and metals and/or metal compounds with an effective amount of at least one fixation chemical to reduce the rate of leaching of said metal and/or metal compounds from said solids.

61. A process for separating extractable organic material from a feed composition comprising an oil-in-water emulsion comprising a continuous aqueous phase, a discontinuous organic phase comprising said extractable organic material, and solids dispersed in said emulsion, the process comprising the steps of:

(I) subjecting feed composition to sufficient shear to convert said feed composition to a water-in-oil emulsion;

(II) contacting said water-in-oil emulsion with at least one first organic solvent, said first organic solvent being capable of forming with said emulsion a system comprising at least two phases and being capable of dissolving at least about ten parts of said extractable organic material per million parts of said first organic solvent at the temperature wherein at least about 50% by weight of said first organic solvent boils at atmospheric pressure; forming a system comprising at least two phases, one of said phases being an emulsion phase comprising said emulsion and the other of said phases being a solvent phase comprising said solvent; extracting at least part of said extractable organic material with part of said solvent, the extracted extractable organic material being dispersed in said solvent phase; separating said emulsion phase from said solvent phase; separating an effective amount of said first organic solvent from said separated emulsion phase to cause separation of said separated emulsion phase into an organic-rich phase and a water-rich phase; and separating said organic-rich phase from said water-rich phase, the solids in said organic-rich phase and/or said water-rich phase being intermixed with at least part of said extractable organic material; and (III) contacting said solids from step (II) with at least one second organic solvent, said second organic solvent being capable of dissolving at least about ten parts of said extractable organic material per million parts of said second organic solvent at the temperature wherein at least about 50% by weight of said second organic solvent boils at atmospheric pressure; dissolving at least part of said extractable organic material in said second organic solvent to form a solvent-extract mixture; and separating at least part of said solvent-extract mixture from said solids.

62. A process for separating extractable organic material from a feed composition comprising an oil-in-water emulsion comprising a continuous aqueous phase, a discontinuous organic phase comprising said extractable organic material, and solids dispersed in said emulsion, the process comprising the steps of:

(I) subjecting said feed composition to sufficient shear to convert said feed composition to a water-in-oil emulsion;

(II) contacting said water-in-oil emulsion with at least one first organic solvent, said first organic solvent being capable of forming with said emulsion a system comprising at least two phases and being capable of dissolving at least about ten parts of said extractable organic material per million parts of said first organic solvent at the temperature wherein at least about 50% by weight of said first organic solvent boils at atmospheric pressure; forming a system comprising at least two phases, one of said phases being an emulsion phase comprising said emulsion and the other of said phases being a solvent phase comprising said solvent; extracting at least part of said extractable organic material with part of said solvent, the extracted extractable organic material being dispersed in said solvent phase; separating said emulsion phase from said solvent phase; separating an effective amount of said first organic solvent from said separated emulsion phase to cause separation of said separated emulsion phase into an organic-rich phase and a water-rich phase; and separating said organic-rich phase from said water-rich phase, the solids in said organic phase and/or said water-rich phase being intermixed with at least part of said extractable organic material;

(III-1) contacting said solids from step (II) with at least one second organic solvent, said second organic solvent being capable of dissolving at least about ten parts of said extractable organic material per million parts of said second organic solvent at the temperature wherein at least about 50% by weight of said second organic solvent boils at atmospheric pressure; dissolving at least part of said extractable organic material in said second organic solvent to form a solvent-extract mixture; and separating at least part of said solvent-extract mixture from said solids to provide an intermediate composition, said intermediate composition comprising said solids and at least part of second organic solvent; and (III-2) contacting said intermediate composition from step (III-1) with at least one third organic solvent, said third organic solvent being more volatile than said second organic solvent and being capable of dissolving at least about ten parts of said second organic solvent per million parts of said third organic solvent at the temperature wherein at least about 50% by weight of said third organic solvent boils at atmospheric pressure; dissolving at least part of said second organic solvent in said third organic solvent to form a solvent-solvent mixture; and separating said solvent-solvent mixture from said intermediate composition.

63. A process for separating extractable organic material from a feed composition comprising an oil-in-water emulsion comprising a continuous aqueous phase, a discontinuous organic phase comprising said extractable organic material, and solids dispersed in said emulsion, the process comprising:

(I) subjecting said feed composition to sufficient shear to convert said feed composition to a water-in-oil emulsion;

(II) contacting said water-in-oil emulsion with at least one first organic solvent, said first organic solvent being capable of forming with said emulsion a system comprising at least two phases and being capable of dissolving at least about ten parts of said extractable organic material per million parts of said first organic solvent at the temperature wherein at least about 50% by weight of said first organic solvent boils at atmospheric pressure; forming a system comprising at least two phases, one of said phases being an emulsion phase comprising said emulsion and the other of said phases being a solvent phase comprising said first organic solvent; extracting at least part of said extractable organic material with part of said solvent, the extracted extractable organic material being dispersed in said solvent phase; separating said emulsion phase from said solvent phase; separating an effective amount of said first organic solvent from said separated emulsion phase to cause separation of said separated emulsion phase into an organic-rich phase and a water-rich phase; and separating said organic-rich phase from said water-rich phase, the solids in said organic-rich phase and/or said water-rich phase being intermixed with at least part of said extractable organic material; and (III) contacting said solids from step (II) with at least one organic solvent mixture, said organic solvent mixture comprising at least one second organic solvent and at least one third organic solvent, said second organic solvent being capable of dissolving at least about ten parts of said extractable organic material per million parts of said second organic solvent at the temperature wherein at least about 50% by weight of said second organic solvent boils at atmospheric pressure, said third organic solvent being more volatile than said second organic solvent and being capable of dissolving at least about ten parts of said second organic solvent per million parts of said third organic solvent at the temperature wherein at least about 50% by weight of said third organic solvent boils at atmospheric pressure; dissolving at least part of said extractable organic material in said organic solvent mixture to form a solvent-extract mixture; and separating at least part of said solvent-extract mixture from said solids.

64. A process for separating extractable organic material from a feed composition comprising an oil-in-water emulsion comprising a continuous aqueous phase, a discontinuous organic phase comprising said extractable organic material, and solids dispersed in said emulsion, the process comprising:

(I) subjecting said feed composition to sufficient shear to convert said feed composition to a water-in-oil emulsion;

(II) contacting said water-in-oil emulsion with at least one first organic solvent, said first organic solvent being capable of forming with said emulsion a system comprising at least two phases and being capable of dissolving at least about ten parts of said extractable organic material per million parts of said first organic solvent at the temperature wherein at least about 50% by weight of said first organic solvent boils at atmospheric pressure; forming a system comprising at least two phases, one of said phases being an emulsion phase comprising said emulsion and the other of said phases being a solvent phase comprising said first organic solvent; extracting at least part of said extractable organic material with part of said solvent, the extracted extractable organic material being dispersed in said solvent phase; separating said emulsion phase from said solvent phase; separating an effective amount of said first organic solvent from said separated emulsion phase to cause separation of said separated emulsion phase into an organic-rich phase and a water-rich phase; and separating said organic-rich phase from said water-rich phase, the solids in said organic-rich phase and/or said water-rich phase being intermixed with at least part of said extractable organic material;

(III-1) contacting said solids from step (II) with at least one organic solvent mixture, said organic solvent mixture comprising at least one second organic solvent and at least one third organic solvent, said second organic solvent being capable of dissolving at least about ten parts of said extractable organic material per million parts of said second organic solvent at the temperature wherein at least about 50% by weight of said second organic solvent boils at atmospheric pressure, said third organic solvent being more volatile than said second organic solvent and being capable of dissolving at least about ten parts of said second organic solvent per million parts of said third organic solvent at the temperature wherein at least about 50% by weight of said third organic solvent boils at atmospheric pressure; dissolving at least part of said extractable organic material in said organic solvent mixture to form a solvent-extract mixture; and separating at least part of said solvent-extract mixture from said solids to form an intermediate composition, said intermediate composition comprising solids and at least part of said second organic solvent; and (III-2) contacting said intermediate composition from step (III-1) with at least one fourth organic solvent, said fourth organic solvent being more volatile than said second organic solvent and being capable of dissolving at least about ten parts of said second organic solvent per million parts of said fourth organic solvent at the temperature wherein at least about 50% by weight of said fourth organic solvent boils at atmospheric pressure; dissolving at least part of said second organic solvent in said fourth organic solvent to form a solvent-solvent mixture; and separating said solvent-solvent mixture from said intermediate composition.

65. A process for separating extractable organic material from a feed composition comprising an oil-in-water emulsion comprising a continuous aqueous phase, a discontinuous organic phase comprising said extractable organic material, and solids dispersed in said emulsion, the process comprising the steps of:

subjecting said feed composition to sufficient shear to convert said feed composition to a water-in-oil emulsion;

contacting said water-in-oil emulsion with at least one first organic solvent, said first organic solvent being capable of forming with said emulsion a system comprising at least two phases and being capable of dissolving at least about ten parts of said extractable organic material per million parts of said first organic solvent at the temperature wherein at least about 50% by weight of said first organic solvent boils at atmospheric pressure; forming a system comprising at least two phases, one of said phases being an emulsion phase comprising said emulsion and the other of said phases being a solvent phase comprising said solvent; extracting at least part of said extractable organic material with part of said solvent, the extracted extractable organic material being dispersed in said solvent phase; separating said emulsion phase from said solvent phase; separating an effective amount of said first organic solvent from said separated emulsion phase to cause separation of said separated emulsion phase into an organic-rich phase and a water-rich phase; and separating said organic-rich phase from said water-rich phase, the solids in said organic-rich phase and/or said water-rich phase being intermixed with at least part of said extractable organic material; and incinerating said solids for an effective period of time to burn off a desired amount of said extractable orgainc material from said solids.

66. A process for separating extractable organic material from a feed composition comprising an oil-in-water emulsion comprising a continuous aqueous phase, a discontinuous organic phase comprising said extractable organic material, and solids dispersed in said emulsion, the process comprising the steps of:

subjecting said feed composition to sufficient shear to convert said feed composition to a water-in-oil emulsion;

contacting said water-in-oil emulsion with at least one first organic solvent, said first organic solvent being capable of forming with said emulsion a system comprising at least two phases and being capable of dissolving at least about ten parts of said extractable organic material per million parts of said first organic solvent at the temperature wherein at least about 50% by weight of said first organic solvent boils at atmospheric pressure; forming a system comprising at least two phases, one of said phases being an emulsion phase comprising said emulsion and the other of said phases being a solvent phase comprising said solvent; extracting at least part of said extractable organic material with part of said solvent, the extracted extractable organic material being dispersed in said solvent phase; separating said emulsion phase from said solvent phase; separating an effective amount of said first organic solvent from said separated emulsion phase to cause separation of said separated emulsion phase into an organic-rich phase and a water-rich phase; and separating said organic-rich phase from said water-rich phase, the solids in said organic-rich phase and/or said water-rich phase being intermixed with at least part of said extractable organic material; and heating said solids in the absence or substantial absence of an oxidant for an effective period of time and at a sufficient temperature to convert said extractable organic material to a product comprising carbon, methane, ethane, ethylene, or a mixture of two or more thereof.

67. A process for separating extractable organic material from a feed composition comprising an oil-in-water emulsion comprising a continuous aqueous phase, a discontinuous organic phase comprising said extractable organic material, and solids dispersed in said emulsion, the process comprising the steps of:

subjecting said feed composition to sufficient shear to convert said feed composition to a water-in-oil emulsion;

contacting said water-in-oil emulsion with at least one first organic solvent, said first organic solvent being capable of forming with said emulsion a system comprising at least two phases and being capable of dissolving at least about ten parts of said extractable organic material per million parts of said first organic solvent at the temperature wherein at least about 50% by weight of said first organic solvent boils at atmospheric pressure; forming a system comprising at least two phases, one of said phases being an emulsion phase comprising said emulsion and the other of said phases being a solvent phase comprising said solvent; extracting at least part of said extractable organic material with part of said solvent, the extracted extractable organic material being dispersed in said solvent phase; separating said emulsion phase from said solvent phase; separating an effective amount of said first organic solvent from said separated emulsion phase to cause separation of said separated emulsion phase into an organic-rich phase and a water-rich phase; and separating said organic-rich phase from said water-rich phase, the solids in said organic-rich phase and/or said water-rich phase being intermixed with at least part of said extractable organic material; and contacting at least part of said water-rich phase with an oxidant at a temperature of about 300° F. to about 1000° F. and a pressure sufficient to maintain said water-rich phase in a liquid or substantially liquid form or in the form of a dense supercritical fluid for an effective period of time to convert a desired amount of the extractable organic material intermixed with said solids to carbon dioxide and water.

68. A process for separating extractable organic material from a feed composition comprising an oil-in-water emulsion comprising a continuous aqueous phase, a discontinuous organic phase comprising said extractable organic material, and solids dispersed in said emulsion, the process comprising the steps of:

(I) subjecting said feed composition to sufficient shear to convert said feed composition to a water-in-oil emulsion; and (II) contacting said feed composition from step (I) with at least one solvent of about 3 to about 7 carbon atoms; forming a system comprising at least two phase systems, one of said phases being an emulsion phase comprising said emulsion and the other of said phases being a solvent phase comprising said solvent; extracting at least part of said extractable organic material with part of said solvent, the extracted extractable organic material being dispersed in said solvent phase; and separating said emulsion phase from said solvent phase.

69. A process for separating extractable organic material from a feed composition comprising an oil-in-water emulsion comprising a continuous aqueous phase, a discontinuous organic phase comprising said extractable organic material, and solids dispersed in said emulsion, the process comprising the steps of:

(I) subjecting said feed composition to sufficient shear to convert said feed composition to a water-in-oil emulsion; and (II) contacting said feed composition from step (I) with at least one solvent comprising propane; forming a system comprising at least two phases, one of said phases being an emulsion phase comprising said emulsion and the other of said phases being a solvent phase comprising said solvent; extracting at least part of said extractable organic material with part of said solvent, the extracted extractable organic material being dispersed in said solvent phase; and separating said emulsion phase from said solvent phase.

* * * * *